United States Patent
Yu et al.

(10) Patent No.: US 10,266,838 B2
(45) Date of Patent: Apr. 23, 2019

(54) METHODS FOR ENHANCING ROOT GROWTH OF PLANTS

(71) Applicant: Academia Sinica, Taipei (TW)

(72) Inventors: Su-May Yu, Taipei (TW); Yi-Shih Chen, Yuanli Township (TW); Shuen-Fang Lo, Taichung County (TW); Tuan-Hua David Ho, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/759,529

(22) PCT Filed: Nov. 21, 2013

(86) PCT No.: PCT/US2013/071340
§ 371 (c)(1),
(2) Date: Jul. 7, 2015

(87) PCT Pub. No.: WO2014/109834
PCT Pub. Date: Jul. 17, 2014

(65) Prior Publication Data
US 2015/0344900 A1   Dec. 3, 2015

Related U.S. Application Data

(60) Provisional application No. 61/729,233, filed on Jan. 8, 2013.

(51) Int. Cl.
*C12N 15/29* (2006.01)
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8271* (2013.01); *C12N 15/8293* (2013.01); *Y02A 40/146* (2018.01)

(58) Field of Classification Search
None
See application file for complete search history.

(56) References Cited

U.S. PATENT DOCUMENTS

| | | | | |
|---|---|---|---|---|
| 2009/0133154 A1* | 5/2009 | Yu | ...................... | C12N 15/8237 800/278 |
| 2009/0193543 A1* | 7/2009 | Sanz Molinero | .. | C12N 15/8261 800/290 |

FOREIGN PATENT DOCUMENTS

| WO | WO 2007-031581 A2 | 3/2007 |
|---|---|---|
| WO | WO 2012-021494 A1 | 2/2012 |

OTHER PUBLICATIONS

Zhao et al. (Acta Physiol Plant (2011) 33:1063-1073).*
Hochholdinger et al. (Current Opinion in Plant Biology 2008, 11:70-74).*
Guo et al. (2004, Proc. Natl. Acad. Sci. USA 101: 9205-9210).*
Zhao et al. (Acta Physiol Plant (2011) 33:1063-1073). (Year: 2011).*
Mulkey et al. "The Kinetics of abscisic acid action on root growth and gravitropism," Planta. Mar. 1, 1983, vol. 157 (2). pp. 150-157.
Tseng et al. "Abscisic Acid- and Stress-Induced Highly Proline-Rich Glycoproteins Regulate Root Growth in Rice," Plant Physiology, Jul. 25, 2013, vol. 163, pp. 118-134.

* cited by examiner

*Primary Examiner* — Elizabeth F McElwain
*Assistant Examiner* — Charles Logsdon
(74) *Attorney, Agent, or Firm* — Wolf, Greenfield & Sacks, P.C.

(57) ABSTRACT

The present invention relates to a method for enhancing root growth of a plant by introducing a polynucleotide encoding late embryogenesis abundant protein, group 3 (LEA3) into the plant. Plant root architecture is essential for its functions in water and nutrient uptake, anchorage and interactions with microbes in the soil.

12 Claims, 20 Drawing Sheets
Specification includes a Sequence Listing.

(A)

*ABRC321*

(A)
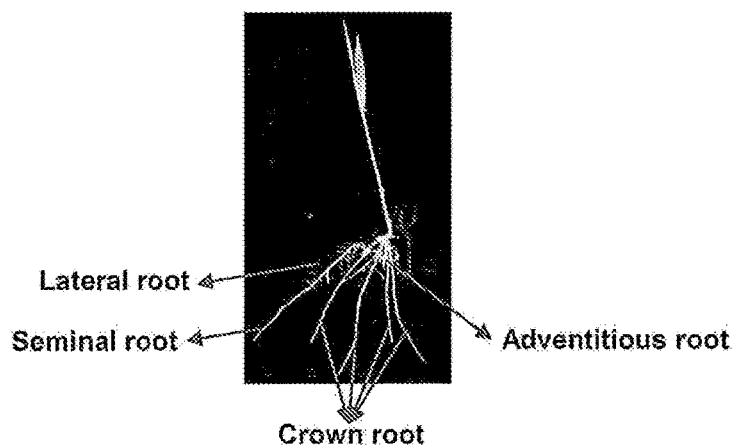
Fig. 6 (Cont')

(A)

(B)

(A)
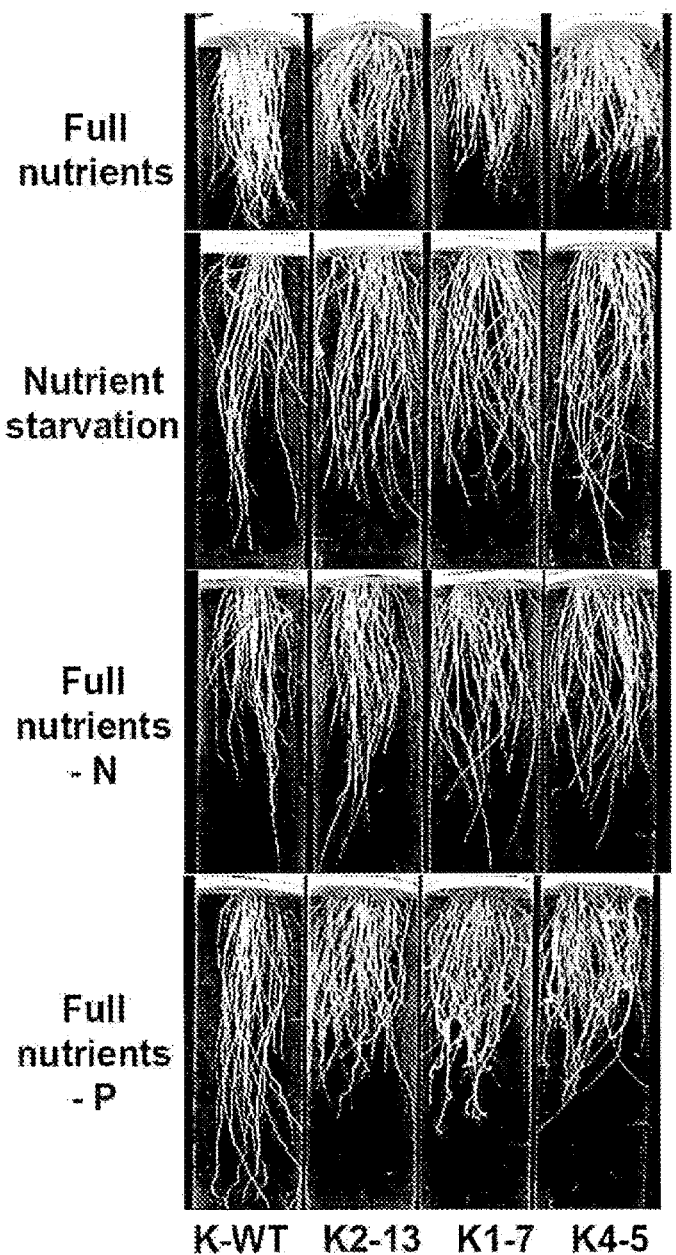
Fig. 8 (Cont')

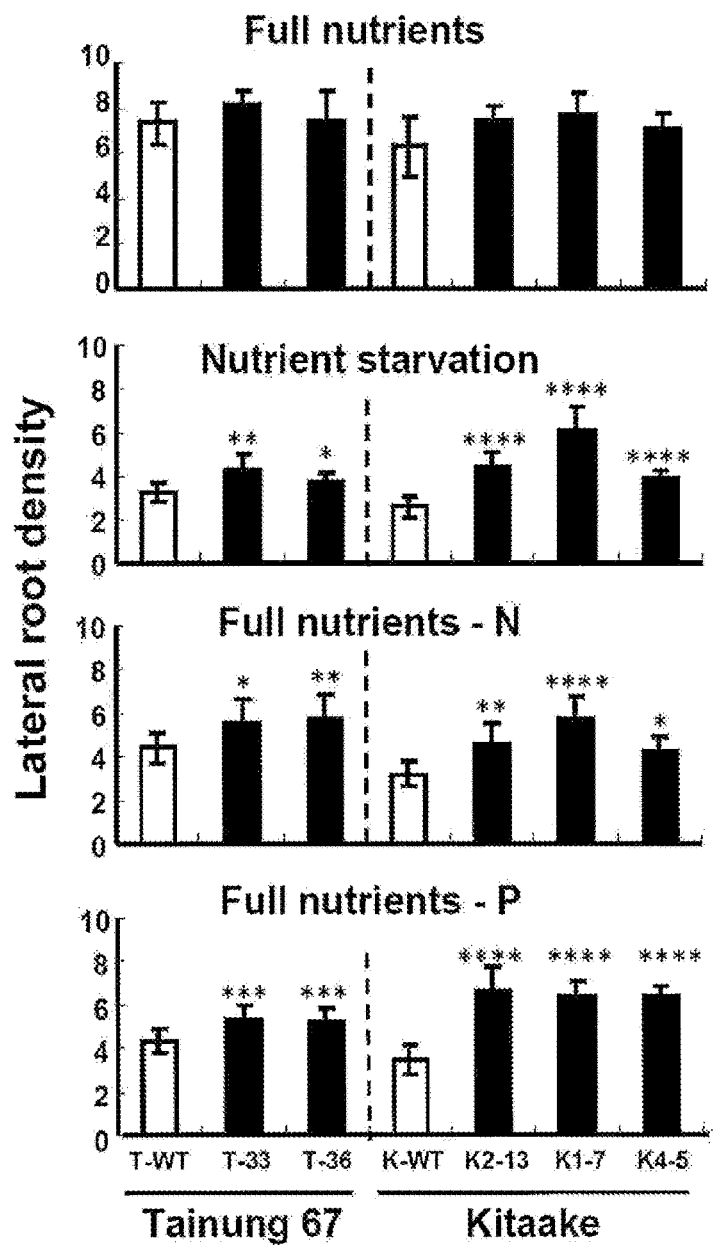
Fig. 8 (Cont')

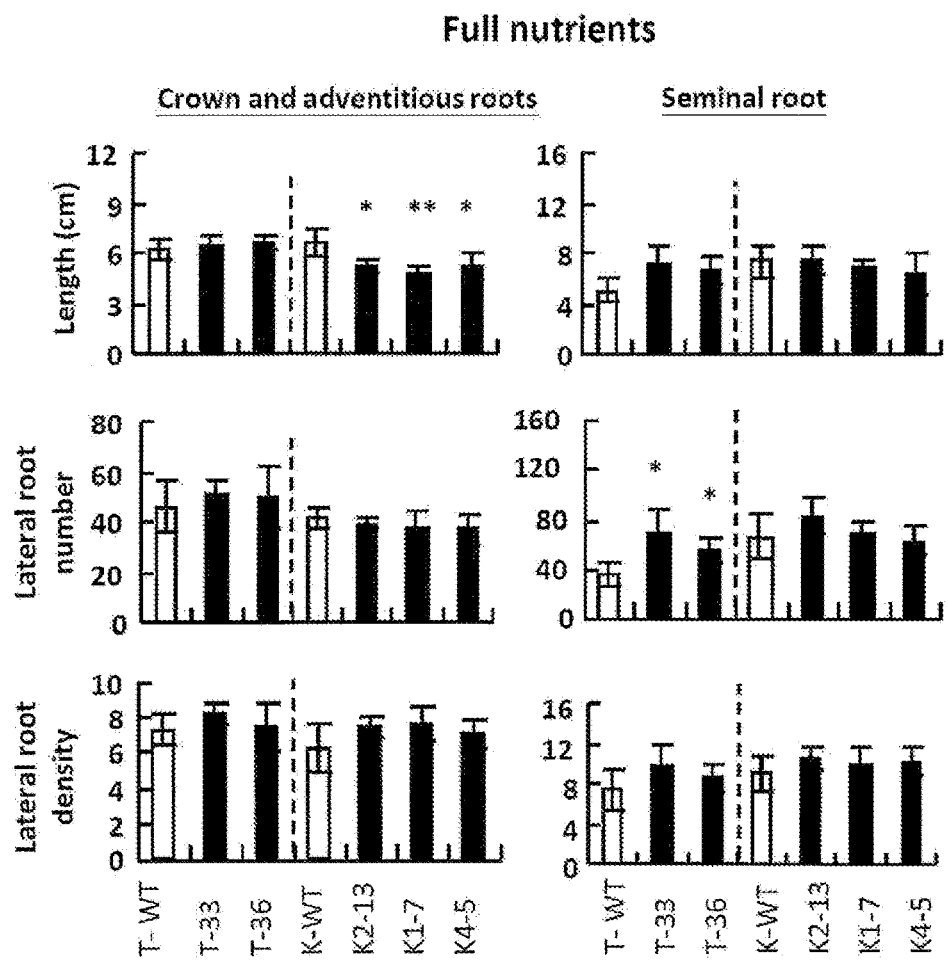
Fig. 9 (Cont')

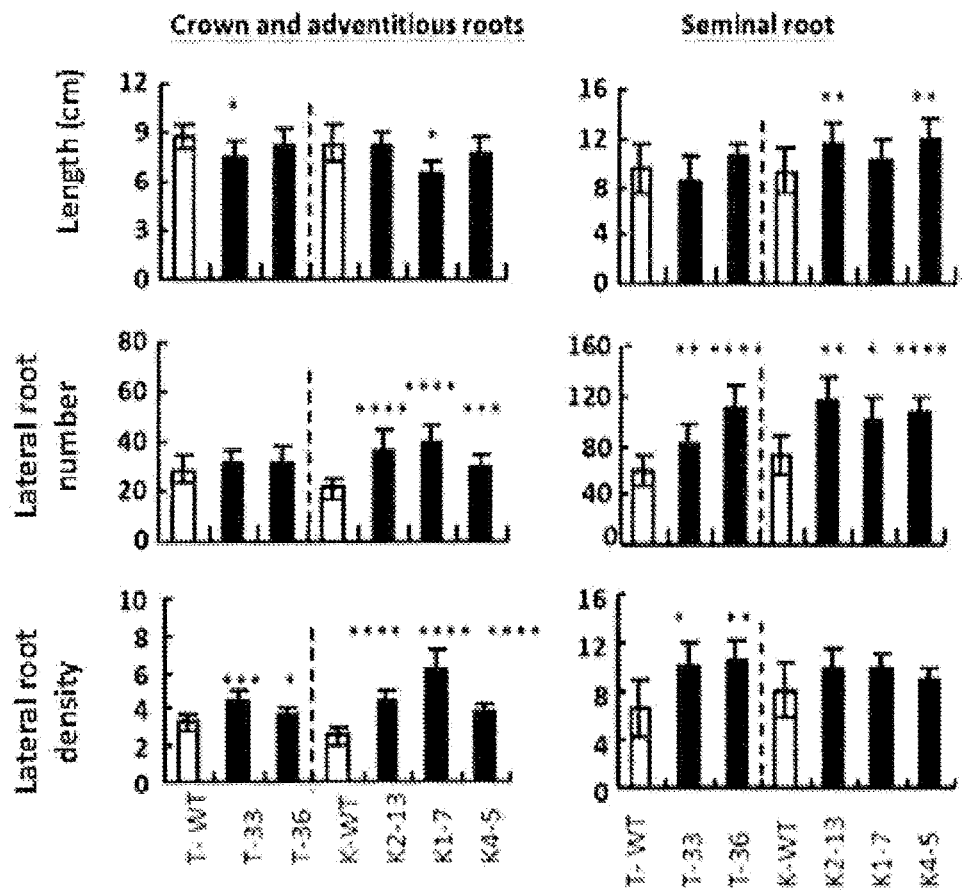
Fig. 9 (Cont')

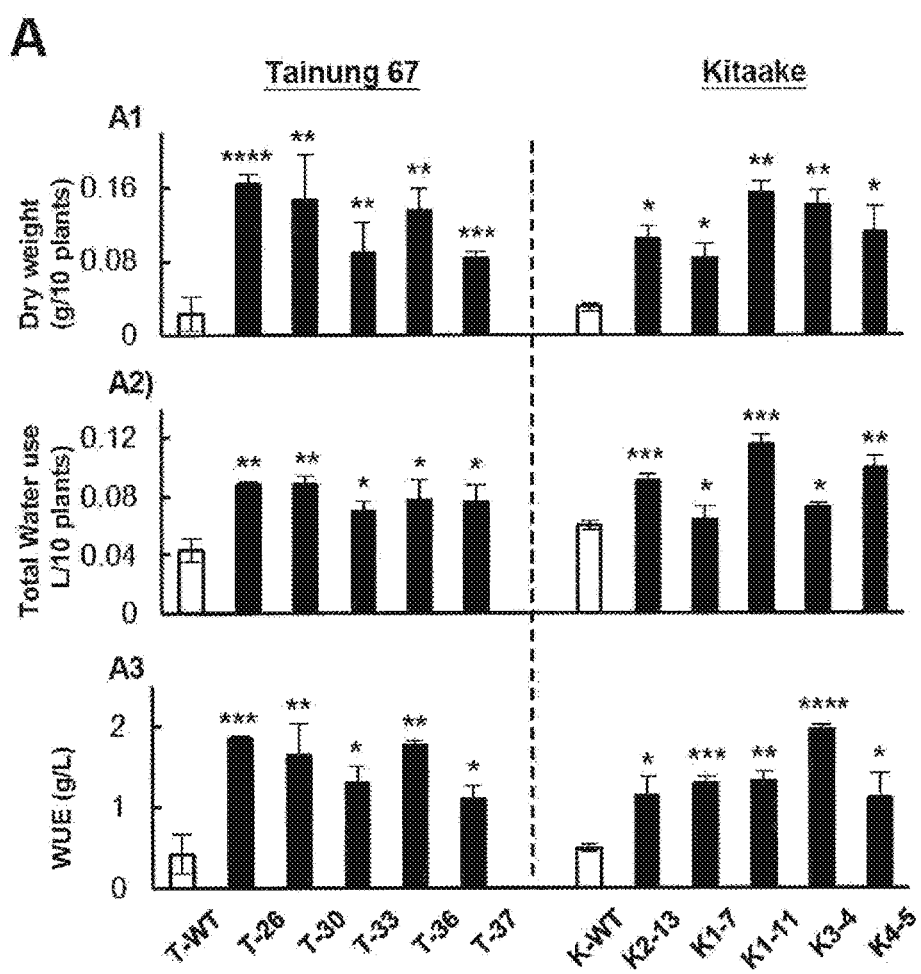
Fig. 13 (Cont')

METHODS FOR ENHANCING ROOT GROWTH OF PLANTS

RELATED APPLICATIONS

This application is a national stage filing under 35 U.S.C. § 371 of international PCT application PCT/US2013/071340, filed Nov. 21, 2013, which claims the benefit of U.S. provisional application No. 61/729,233, filed Jan. 8, 2013, under 35 U.S.C. § 119, each of which is incorporated by reference herein in its entirety.

TECHNOLOGY FIELD

The present invention relates to a method for enhancing root growth of plants. More particularly, the invention relates to a method for enhancing root growth of plants by introducing a polynucleotide encoding group 3 late embryogenesis abundant protein (LEA3) into the plant.

BACKGROUND OF THE INVENTION

Plant root architecture is essential for its functions in water and nutrient uptake, anchorage and interactions with microbes in the soil.

Studies in *Arabidopsis* have greatly advanced our knowledge on mechanisms controlling root development (Potters G et al., (2007) *Trends Plant Sci* 12(3):98-105; Peret B, et al. (2009) *Trends Plant Sci* 14(7):399-408; Lavenus J, et al. (2013) *Trends Plant Sci* 18(8):450-458); however, similar studies in cereals are relatively scarce (Coudert Y et al., (2010) *Trends Plant Sci* 15(4):219-226). Unlike *Arabidopsis* which has a primary root that iteratively branches to generate several orders of lateral roots, the cereals have several types of branched roots including shoot-born crown roots and root-borne lateral roots. Approximately 675 quantitative trait loci (QTLs) control 29 root parameters in rice (Courtois B, et al. (2009) *Rice* 2(2-3):115-128). Several homologous genes that play similar roles regulating root formation between *Arabidopsis* and cereals have been identified; however, distinct hormonal and developmental pathways are also found to be involved in root formation in cereals (Orman-Ligeza B, et al. (2013) *Trends Plant Sci* 18(8):459-467). In *Arabidopsis*, six classical hormones control primary root growth by targeting cells in distinct tissues (Ubeda-Tomas S et al., (2012) *Trends Plant Sci* 17(6):326-331). Among these hormones, auxin is shown to act as a common integrator to many endogenous and environmental signals regulating lateral root development in both dicots and monocots (Ubeda-Tomas S et al., supra; Laurie S et al., *J Exp Bot* 54(383):739-747). In *Arabidopsis*, the universal stress hormone abscisic acid (ABA) stimulates main root elongation in response to drought and osmotic stresses; however, ABA and auxin signals act antagonistically during lateral root initiation, with ABA as a repressing while auxin a promoting agent (De Smet I et al., (2006) *Trends Plant Sci* 11(9):434-439).

LEA proteins are a set of proteins highly accumulated at the onset of seed desiccation and in response to water deficit in plant vegetative tissues (Dure L (1981) *Biochemistry* 20:4162-4168; Dure L (1992) *Control of Plant Gene Expression*. CRC Press, Boca Raton, Fla., pp. 325-335). LEA proteins have been classified into six groups based on conservation in amino acid sequence domains and expression patterns (Dure L, 3rd (1993) *Plant J* 3(3):363-369; Wise M J (2003) *BMC Bioinformatics* 4:52) HVA1 is a group 3 LEA (LEA3) protein specifically expressed in barley aleurone layers and embryos during late seed development undergoing desiccation (Jefferson R A (1987) *Plant Mol Biol Rep* 5:387-405). HVA1 contains an 11-amino acid consensus motif which is repeated 9 times, forming an α-helical dimmer suitable for accommodating positively and negatively charged ions, thus has been proposed to function as an ion sequester (Liang Y & Harris J M (2005) *Am J Bot* 92(10):1675-1683). Functions of HVA1 in protection against environmental stresses have been reported (Hong B et al., (1992) *Plant Mol Biol* 18:663-674; Sutton F et al., *Plant Physiol* 99(1):338-340). However, no one reports HVA1's function on promoting root growth of plants.

BRIEF SUMMARY OF THE INVENTION

In the present invention, it is unexpectedly found that a transgenic plant transformed with group 3 late embryogenesis abundant protein (LEA3) gene exhibits surprisingly improved root growth as compared with a control (wild type) plant without transformation with LEA3 gene. Compared with control plants, the transgenic plants of the invention exhibit significant increase in elongation, number, and density of primary and branch root system and initiation of lateral root. Especially, the transgenic plants exhibit improved root growth in the presence of stress hormone abscisic acid (ABA) or under nutrient deficient conditions.

Therefore, the present invention provides a method for enhancing root growth of a plant, comprising (i) introducing a polynucleotide encoding group 3 late embryogenesis abundant protein (LEA3) into a plant cell to obtain a transformed plant cell, wherein the polynucleotide is operably linked to an expression control sequence;

(ii) producing a transformed plant from said transformed plant; and (iii) selecting a transformed plant exhibiting improved root growth compared to a control plant which is not introduced with the polynucleotide.

In some certain embodiments, the expression control sequence comprising a promoter sequence, which is selected from the group consisting of SEQ ID NO: 1, SEQ ID NO: 2 and SEQ ID NO: 3, preferably SEQ ID NO: 3.

In some certain embodiments, the LEA3 protein is the one originated from barely or rice, for example, having the amino acid sequence of SEQ ID NO: 4 or 5.

In some certain embodiments, the transgenic plant is monocotyledon, including but not limited to rice, barley, wheat, rye, oat, corn, bamboo, sugar cane, onion, leek and ginger.

In some certain embodiments, the transgenic plant is dicotyledon, including but not limited to *Arabidopsis*, eggplant, soybean, mung bean, kidney bean, pea, tobacco, lettuce, spinach, sweet potato, carrot, melon, cucumber and pumpkin.

To perform the method of the invention, it is preferably to select the transgenic plants with improved root growth, in the presence of stress hormone abscisic acid (ABA) or under nutrient deficient conditions.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 4 shows that amino acid sequence of barley HVA1 (SEQ ID NO: 4) is homologous to that of the rice LEA3 (SEQ ID NO: 5). Amino acid alignment of barley HVA1 and rice LEA3 was performed using Vector NTI 9.0 software and the consensus sequence (SEQ ID NO:7) was identified. The light gray and dark gray highlights indicate identical and similar amino acid sequences, respectively. The underline indicates the tandem 11-mer conserved amino acid repeats.

DETAILED DESCRIPTION OF THE INVENTION

Figure 1:
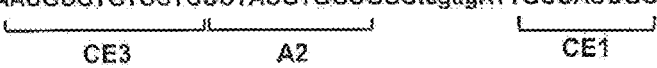
FIG. 1 shows (A) the nucleotide sequence of ABRC321 (SEQ ID NO: 1)_containing CE3 and A2 from HVA1 ABRC3 and CE1 from HVA22 ABRC1; (B) constructs contain 0-3 tandem repeats of ABRC321 for GUS expression (the lengths of DNA fragments constituting the expression cassette being: ABRC321 (including ABRE, linker and enzyme restriction sites), 56 bp; Amy64 minimal promoter (mini P), 99 bp; Intron1-exon2-intron2 (In1-Ex2-In2) of HVA22, 240 bp; GUS cDNA, 2 kb; HVA22 terminator (3'), 120 bp; and (C) constructs containing 3 tandem repeats of ABRC321 for rHVA1 expression (lengths of HVA1 cDNA and Nos 3' being 630 and 300 bp, respectively, SEQ ID NO: 6).
Figure 1:
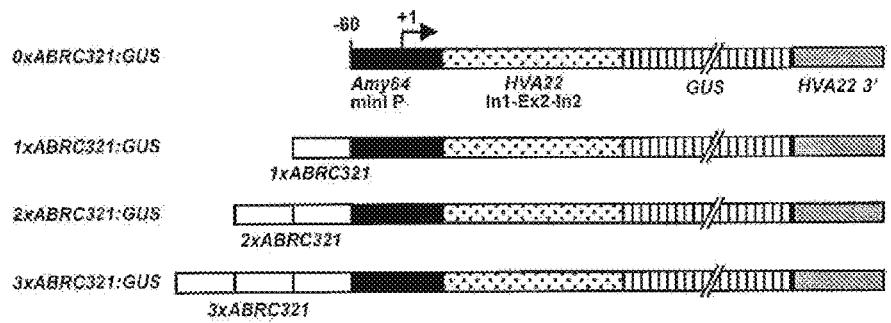
Figure 1:
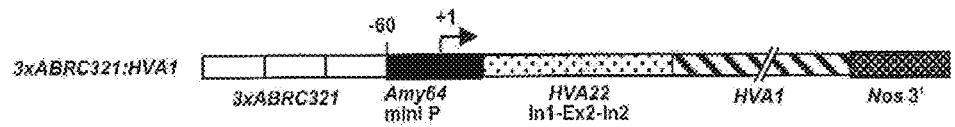

Unless defined otherwise, all technical and scientific terms used herein have the same meanings as is commonly understood by one of skill in the art to which this invention belongs.

As used herein, the articles "a" and "an" refer to one or more than one (i.e., at least one) of the grammatical object of the article. By way of example, "an element" means one element or more than one element.

The term "polynucleotide" or "nucleic acid" refers to a polymer composed of nucleotide units. Polynucleotides include naturally occurring nucleic acids, such as deoxyribonucleic acid ("DNA") and ribonucleic acid ("RNA") as well as nucleic acid analogs including those which have non-naturally occurring nucleotides. Polynucleotides can be synthesized, for example, using an automated DNA synthesizer. The term "nucleic acid" typically refers to large polynucleotides. It will be understood that when a nucleotide sequence is represented by a DNA sequence (i.e., A, T, G, C), this also includes an RNA sequence (i.e., A, U, G, C) in which "U" replaces "T." The term "cDNA" refers to a DNA that is complementary or identical to an mRNA, in either single stranded or double stranded form.

The term "complementary" refers to the topological compatibility or matching together of interacting surfaces of two polynucleotides. Thus, the two molecules can be described as complementary, and furthermore the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'."

The term "encoding" refers to the inherent property of specific sequences of nucleotides in a polynucleotide (e.g., a gene, a cDNA, or an mRNA) to serve as templates for synthesis of other polymers and macromolecules in biological processes having either a defined sequence of nucleotides (i.e., rRNA, tRNA and mRNA) or a defined sequence of amino acids and the biological properties resulting therefrom. Therefore, a gene encodes a protein if transcription and translation of mRNA produced by that gene produces the protein in a cell or other biological system. It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "recombinant nucleic acid" refers to a polynucleotide or nucleic acid having sequences that are not naturally joined together. A recombinant nucleic acid may be present in the form of a vector. "Vectors" may contain a given nucleotide sequence of interest and a regulatory sequence. Vectors may be used for expressing the given nucleotide sequence or maintaining the given nucleotide sequence for replicating it, manipulating it or transferring it between different locations (e.g., between different organisms). Vectors can be introduced into a suitable host cell for the above mentioned purposes.

As used herein, the term "operably linked" may mean that a polynucleotide is linked to an expression control sequence in such a manner to enable expression of the polynucleotide when a proper molecule (such as a transcriptional factor) is bound to the expression control sequence.

As used herein, the term "expression control sequence" or "regulatory sequence" means a DNA sequence that regulates the expression of the operably linked nucleic acid sequence in a certain host cell.

Examples of vectors include, but are not limited to, plasmids, cosmids, phages, YACs or PACs. Typically, in vectors, the given nucleotide sequence is operatively linked to the regulatory sequence such that when the vectors are introduced into a host cell, the given nucleotide sequence can be expressed in the host cell under the control of the regulatory sequence. The regulatory sequence may comprises, for example and without limitation, a promoter sequence (e.g., the cytomegalovirus (CMV) promoter, simian virus 40 (SV40) early promoter, T7 promoter, and alcohol oxidase gene (AOX1) promoter), a start codon, a replication origin, enhancers, an operator sequence, a secretion signal sequence (e.g., α-mating factor signal) and other control sequence (e.g., Shine-Dalgano sequences and termination sequences). Preferably, vectors may further contain a marker sequence (e.g., an antibiotic resistant marker sequence) for the subsequent screening procedure. For purpose of protein production, in vectors, the given nucleotide sequence of interest may be connected to another nucleotide sequence other than the above-mentioned regulatory sequence such that a fused polypeptide is produced and beneficial to the subsequent purification procedure. Said fused polypeptide includes, but is not limited to, a His-tag fused polypeptide and a GST fused polypeptide.

Where the expression vector is constructed for a plant cell, several suitable promoters known in the art may be used, including but not limited to the Figwort mosaic virus 35S promoter, the cauliflower mosaic virus (CaMV) 35S promoter, the commelina yellow mottle virus promoter, the rice cytosolic triosephosphate isomerase (TPI) promoter, the rice actin 1 (Act1) gene promoter, the uniquitin (Ubi) promoter, the rice amylase gene promoter, the adenine phosphoribosyltransferase (APRT) promoter of *Arabidopsis*, the mannopine synthase and octopine synthase promoters.

In certain embodiments, a promoter sequence as used in the invention is a synthetic promoter, having SEQ ID NO: 1 (1xABRC321), SEQ ID NO: 2 (2xABRC321) or SEQ ID NO: 3 (3xABRC321), preferably SEQ ID NO: 3 (3xABRC321).

To prepare a transgenic plant, it is preferably that the expression vector as used herein carries one or more selection markers for selection of the transformed plants, for example, genes conferring the resistance to antibiotics such as hygromycin, ampicillin, gentamycine, chloramphenicol, streptomycin, kanamycin, neomycin, geneticin and tetracycline, URA3 gene, genes conferring the resistance to any other toxic compound such as certain metal ions or herbicide, such as glufosinate or bialaphos.

As used herein, the term "transgenic plant" or "transgenic line" refers to a plant that contains a recombinant nucleotide sequence. The transgenic plant can be grown from a recombinant cell.

A variety of procedures that can be used to engineer a stable transgenic plant are available in this art. In one embodiment of the present invention, the transgenic plant is produced by transforming a tissue of a plant, such as a protoplast or leaf-disc of the plant, with a recombinant Agrobacterium cell comprising a polynucleotide encoding a desired protein (e.g. LEA3) and generating a whole plant from the transformed plant tissue. In another embodiment, a polynucleotide encoding a desired protein can be introduced into a plant via gene gun technology, particularly if transformation with a recombinant Agrobacterium cell is not efficient in the plant.

The term "polypeptide" refers to a polymer composed of amino acid residues linked via peptide bonds. The term "protein" typically refers to relatively large polypeptides. The term "peptide" typically refers to relatively short polypeptides.

As used herein, LEA3 protein is group 3 LEA proteins that are a set of proteins highly accumulated at the onset of seed desiccation and in response to water deficit in plant vegetative tissues. HVA1 is a LEA3 protein in barley, which has been identified to have an 11-amino acid consensus motif which is repeated 9 times, forming an α-helical dimer suitable for accommodating positively and negatively charged ions. In certain embodiments, the LEA3 protein as used herein is the one originated from barely (HVA1) or rice (OsLEA3), particularly have the amino acid sequence of SEQ ID NO: 4 or 5.

It is understandable that the LEA3 protein as used herein also include its biological equivalent, which means that there is a limited number of changes or modifications that may be made within a certain portion of the molecule irrelevant to the activity or function of the protein and still result in a molecule with an acceptable level of equivalent biological activity. Biologically equivalent polypeptides are thus defined herein as those polypeptides in which certain amino acid residues may be substituted. Polypeptides with different substitutions may be made and used in accordance with the invention. Modifications and changes may be made in the structure of such polypeptides and still obtain a molecule having similar or desirable characteristics. For example, certain amino acids may be substituted for other amino acids in the peptide/polypeptide structure without appreciable loss of activity. Amino acid substitutions are generally based on the relative similarity of the amino acid side-chain substituents, for example, their hydrophobicity, hydrophilicity, charge, size, and the like. For example, arginine (Arg), lysine (Lys), and histidine (His) are all positively charged residues; and alanine (Ala), glycine (Gly) and serine (Ser) are all in a similar size. Therefore, based upon these considerations, arginine (Arg), lysine (Lys) and histidine (His); and alanine (Ala), glycine (Gly) and serine (Ser) may be defined as biologically functional equivalents. One can readily design and prepare recombinant genes for microbial expression of polypeptides having equivalent amino acid residues.

In some embodiments, the biological equivalent of LEA3 protein comprises the amino acid sequence having at least 50%, 60%, or 65%, or 70%, or 75%, or 80%, or 85%, or 90%, or 95% identity with the amino acid sequence of SEQ ID NO: 4 or 5, and possess the conserved structure, i.e. an 11-amino acid consensus motif, which is repeated 9 or more times (such as 10 to 25 repeats, 10 to 20 repeats, or 10 to 15 repeats), forming an α-helical dimer suitable for accommodating positively and negatively charged ions.

To determine the percent identity of two amino acid sequences, the sequences are aligned for optimal comparison purposes (e.g., gaps can be introduced in the sequence of a first amino acid sequence for optimal alignment with a second amino acid sequence). In calculating percent identity, typically exact matches are counted. The determination of percent homology or identity between two sequences can be accomplished using a mathematical algorithm known in the art, such as BLAST and Gapped BLAST programs, the NBLAST and XBLAST programs, or the ALIGN program.

As used herein, the term "improved root growth" refers to the growth of root system of a transgenic plant is improved or enhanced when compared with a control plant that is not introduced with the same gene. Such improvement, for example, includes one or more characteristics of roots, e.g. increase in total number, length, density, dry weight and initiation, of primary root or secondary root, or crown root, lateral root, adventitious root, or seminal root.

The present invention is based on the unexpected finding that transformation of LEA3 gene into a plant surprisingly promotes the root growth in the plant when compared with a control plant that is not introduced with the gene.

Therefore, the present invention provides a method for enhancing root growth of a plant, comprising
(i) introducing a polynucleotide encoding group 3 late embryogenesis abundant (LEA3) protein into a plant cell to obtain a transformed plant cell, wherein the polynucleotide is operably linked to an expression control sequence;
(ii) producing a transformed plant from said transformed plant; and
(iii) selecting a transformed plant exhibiting improved root growth compared to a control plant which is not introduced with the polynucleotide.

According to the invention, the LEA3 protein can be the one originated from monocotyledon or dicotyledon.

Examples of monocotyledon includes but not limited to rice, barley, wheat, rye, oat, corn, bamboo, sugar cane, onion, leek and ginger.

Examples of monocotyledon includes but not limited to Arabidopsis, eggplant, soybean, mung bean, kidney bean, pea, tobacco, lettuce, spinach, sweet potato, carrot, melon, cucumber and pumpkin.

In particular examples, the LEA3 protein is the one from barley and rice, more particularly having the amino acid sequence of SEQ ID NO: 4 or 5.

According to the present invention, the transgenic plants transformed with the LEA3 gene surprisingly exhibit improved root growth, even without ABA treatment, and have more significant improvement of root growth under ABA induction.

Therefore, in one certain embodiment, it is preferably to select the transgenic plants improved root growth, in the presence of ABA. Particularly, ABA is applied at a concentration from 0.1 to 5 µM, more particularly, from 0.1 to 2 µM, even more particularly from 0.1 to 0.5 µM.

It is also found that the transgenic plants transformed with the LEA3 gene exhibit improved root growth under nutrient deficient conditions.

As known in the art, normal nutrients of plant include major nutrients required in largest amount in plants, including nitrogen (N), phosphorus (P), potassium (K), calcium (Ca), magnesium (Mg) and sulfur (S), and minor nutrients required in relatively smaller amount, including iron (Fe), copper (Cu), zinc (Zn), boron (B), molybdenum (Mo), manganese (Mn) and chlorine (Cl). Additional mineral elements that are good for plants but not necessarily essential include sodium (Na), cobalt (Co), vanadium (Va), nickel (Ni), selenium (Se), aluminum (Al) and silicon (Si). In one embodiment, for hydroponic culture of rice seedlings, a commercial product, Yoshida's culture solution can be used, for example see From IRRI (1976) Laboratory Manual for Physiological Studies of Rice. As used herein, nutrient deficient conditions for plants refers to a condition lacking one or more chemical elements for plant growth, such as lacking one or more of those as set forth above, particularly the major nutrients, e.g. nitrogen (N), phosphorus (P), potassium (K), calcium (Ca), magnesium (Mg) and sulfur (S), more particularly nitrogen (N), phosphorus (P), potassium (K), calcium (Ca), magnesium (Mg), and even more particularly nitrogen (N), phosphorus (P) and potassium (K), and/or the minor nutrients, e.g. iron (Fe), copper (Cu), zinc (Zn), boron (B), molybdenum (Mo), manganese (Mn) and chlorine (Cl), and/or additional mineral elements, e.g. sodium (Na), cobalt (Co), vanadium (Va), nickel (Ni), selenium (Se), aluminum (Al) and silicon (Si). In some embodiments, nutrient deficient conditions also mean that the concentration of the chemical elements as set forth above is overly low, for example, less than 80%, 70%, 60%, 50%, 40%, 30%, 20%, or 10% of regular amount of total nutrients or each nutrient element as required for plant growth.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

1. Materials and Methods 1.1 Plant Materials

Rice cultivars *Oryza sativa* L. cv Tainung 67 and *Oryza sativa* L. cv Kitaake were used for all experiments. Plasmid was introduced into *Agrobacterium tumefaciens* strain EHA101 and rice transformation was performed as described (Chen P-W, et al. (2002) *J Biol Chem* 277:13641-13649). Homozygous transgenic lines were used in all experiments. For observation of root growth, transgenic rice seeds were germinated on the surface of half-strength MS medium without sugar but with or without ABA. For hydroponic culture, Yoshida solution was used. Seedlings were normally grown in 28'C incubator with 12 hr daily light.

1.2 Plasmids

Plasmid pAHC18 contains the luciferase (Luc) cDNA fused between the Ubi promoter and the Nos terminator (Bruce W B et al., (1989) *Proc Natl Acad Sci USA* 86(24): 9692-9696). Plasmid MP64 contains the barley Amy64 minimal promoter (−60 relative to the transcription start site) and its 5' untranslated region (+57 relative to the transcription start site), HVA22 intron1-exon2-intron2, the GUS coding region, and the HVA22 3'untranslated region (Shen Q & Ho T H (1995) *Plant Cell* 7(3):295-307). Plasmid QS 115 contains a copy of HVA22 ABRC1 fused upstream of the Amy64 minimal promoter in plasmid MP64 (Shen Q & Ho T H, supra).

1.3 Plasmid Construction

Two 56-bp complementary oligonucleotides, containing the CE3 and A2 elements from the HVA1 promoter and the CE1 element from the HVA22 promoter (Shen Q, Zhang P, & Ho T H (1996) *Plant Cell* 8(7):1107-1119) and restriction sites KpnI, XhoI and XbaI were synthesized, annealed, and designated as ABRC321 (FIG. 1A). ABRC321 was self-ligated in two or three copies in correct orientations. For expression of GUS under the control of ABRC321, 1-3 copies ABRC321 was inserted into the XbaI site in MP64, so that the ABRC321 was fused upstream of the barley Amy64 minimal promoter, generating constructs 1xABRC321-GUS, 2x-ABRC321-GUS and 3xABRC321-GUS (FIG. 1(B)). For expression of HVA1 under the control of 3xABRC321, GUS cDNA in construct 3xABRC321-GUS was replaced with HVA1 cDNA, generating construct 3xABRC321-HVA1 (FIG. 1(C)) (SEQ ID NO: 6).

1.4 GUS Activity Staining

Sections of leaf and root from 10-day-old seedlings were cut with Microslicers DTK-1000 (TED PELLA, Inc.), incubated in water containing or lacking 10 µM ABA at 28° C. for 24 h, and subjected to histochemical staining with a buffer (0.1 M $NaPO_4$, pH 7.0, 10 mM EDTA, 0.1% Triton X-100, 0.5 mM potassium ferricyanide, pH 7.0 and 1 mM X-glucuronide) at 37° C. as described (Jefferson R A (1987) *Plant Mol Biol Rep* 5:387-405). After GUS staining, leave samples were incubated in 70% ethanol at 65° C. for 1 h to remove chlorophyll.

1.5 Immuno-Histological Fluorescence Staining

Tissue localization of HVA1 was examined by modification of a described method (Long S P et al., (2006) *Plant Cell Environ* 29(3):315-330). Rice roots were fixed with 2% paraformaldehyde (w/v) in 0.1 M $NaPO_4$ buffer, pH 7.0, and then embedded in 5% agar. Sections were sliced to 30-um thickness using Microslicers DTK-1000 and incubated in PBS buffer containing 0.3% (v/v) Triton X-100 (PBS-T). The nonspecific reaction was blocked with 5% (w/v) bovine serum albumin in PBS-T. Samples were then incubated with purified rabbit anti-barley HVA1 polyclonal antibodies and subsequently with secondary antibodies (Alexa Fluor 555 goat anti-rabbit IgG; Molecular Probes). Samples were examined with a laser scanning confocal microscope. (LSM510 META; Zeiss).

1.6 Measurement of Roots

Rice branch roots could be classified into four types: seminal root, also called radical, the first root grows during germination; crown roots, roots emerge from the node of coleoptile; adventitious roots, roots differentiate from the nodes of main stem and tillers, lateral roots, roots branch from above three types of roots and can bear additional large or small lateral roots until the fifth order of branching. The number of each type of root was measured by simple counting. Root length was measured, number of roots was counted, and lateral root density was determined by dividing lateral root number with root length. Error bars represent SD (n=12). Significance levels: *$P<0.05$, $P<0.01$, *$P<0.001$.

1.7 Field Test

To evaluate grain yield and biomass production in the field, 25-day-old seedlings were transplanted to field with 25×25 cm of space between each plant. Irrigated field was flooded with 1-5 cm of water (soil water content 37%, v/v) until the end of active tillering stage (30-40 days after transplanting), then water was drained (soil water content 27%, v/v) for 10-15 days at late tillering stage, and flooded again with 3-10 cm of water until the milky stage. Soil in the non-irrigated field was kept moist (soil water content 20-25%, v/v) by intermittent irrigation during the entire planting period. Soil water content was measured using a Theta probe and meter (models ML2x and HH1, Delta-T devices, Cambridge, UK) (Ji K, et al. (2012) *J Plant Physiol* 169(4):336-344). Seeds were harvested, dried and yield determined.

Figure 2:
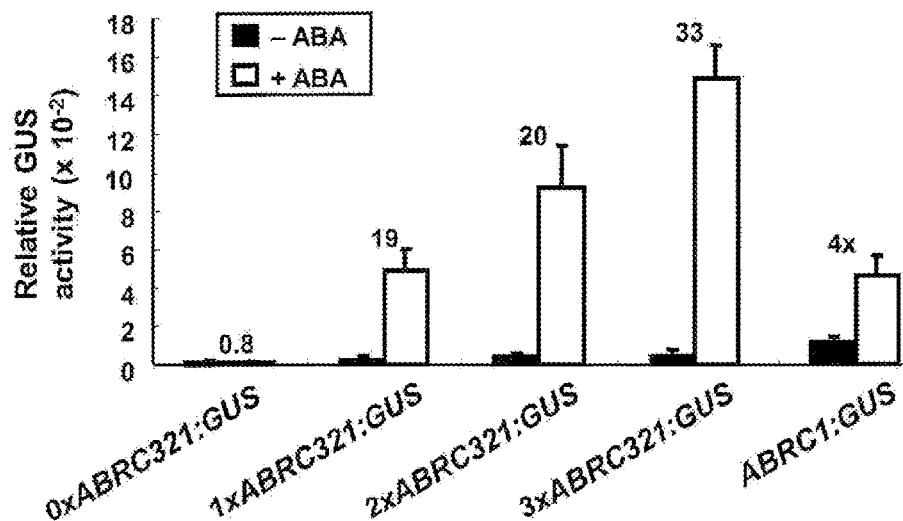
FIG. 2 shows that ABRC321 is an ABA-inducible synthetic promoter with low-background but high ABA-inducible activity in leaves and roots in transgenic rice. (A) Three copies of ABRC321 confer high ABA inducibility in a rice half-seed transient expression assay. Rice half seeds were transfected with plasmids shown in FIG. 1 by particle bombardment, and incubated with (+) or without (−) 10 μM ABA for 16 h, and GUS activity was analyzed. (B) Three copies of ABRC321 confer high ABA inducibility in leaves and roots in transgenic rice. Constructs shown in FIG. 1 were introduced into the rice genome. Leaves and roots of 10-day-old T2 seedlings of four transgenic lines were collected and incubated in water with (+) or without (−) 10 μM ABA for 16 h, and GUS activity was analyzed. Numbers above bars indicate fold induction of GUS activity by ABA. Error bars represent SD (n=3).
Figure 2:
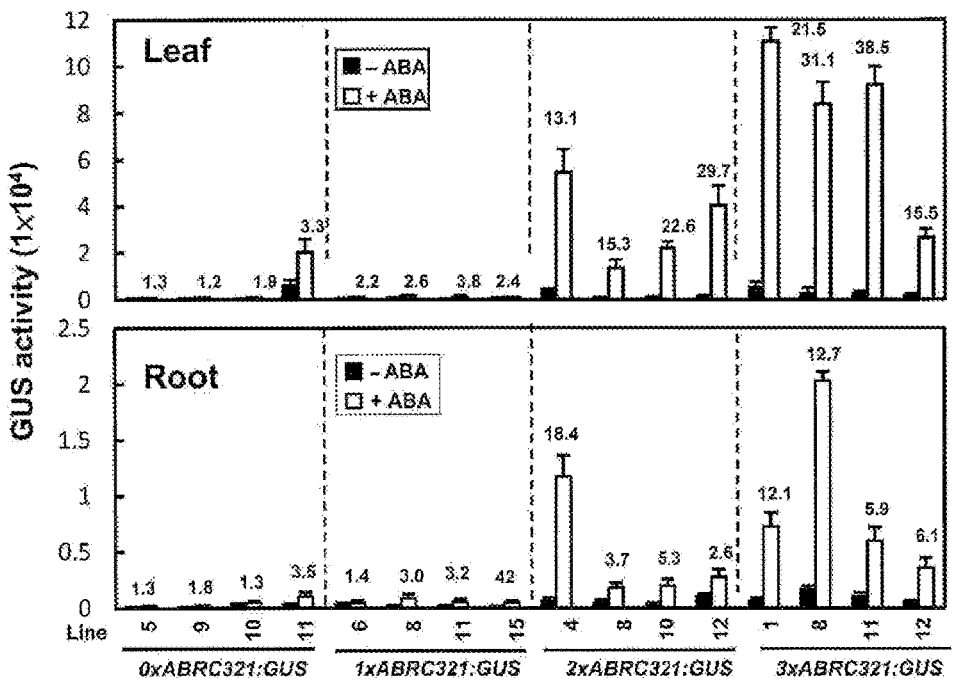

2. Results 2.1 ABRC321 has Low-Background but High ABA-Inducibility in Leaves and Roots in Transgenic Rice In this study, we used a tissue specific promoter, ABRC321, to express recombinant HVA1 (rHVA1) in plants. FIG. 1(A) shows the sequence of ABRC321. ABRC321 was generated by fusion of coupling element CE3 and ABRE2 (A2) from the HVA1 ABRC3 and coupling element CE1 from the HVA22 ABRC1 (Shen Q, Zhang P, & Ho T H (1996) *Plant Cell* 8(7):1107-1119). The reporter gene GUS was fused downstream of 1-3 tandem repeats of ABRC321 and the Amy64 minimal promoter. See FIG. 1 (B). Without ABA treatment, GUS activity was relatively low and only slightly increased with the copy number of ABRC321; in contrast, with ABA, GUS activity controlled by 1xABRC321, 2xABRC321 and 3xABRC321 was induced by 19-, 20-, and 33-fold, respectively (FIG. 2 (A)).

All ABRC321:GUS constructs were also used for rice stable transformation. As shown in FIG. 2(B), four representative transgenic lines for each construct exhibited positional effects of transgene insertion site on absolute promoter activities. Among them, the GUS activity in leaves and roots controlled by 3xABRC321 was most highly induced by ABA among all constructs, and its absolute level and fold induction were generally higher in leaves than in roots in response to ABA. These studies show that the promoter activity of 3xABRC321 in vegetative tissues have relatively low background but is highly inducible by ABA.

Figure 3:
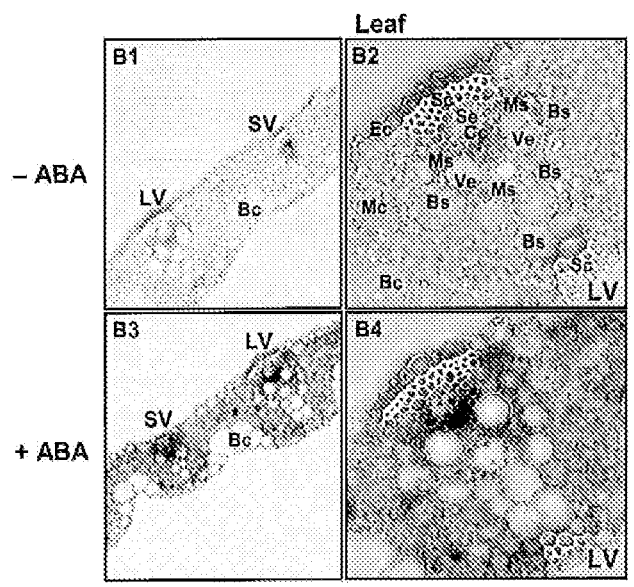
FIG. 3 shows that 3xABRC321 has low-background but high ABA-inducibility in leaves (A) and roots (B) in transgenic rice. (B1) and (B2): without ABA treatment; (B3) and (B4): with ABA treatment. Abbreviation for leaf tissues: Bc: bulliform cell; Bs: bundle sheath; Cc: companion cell; Ec: epidermal cell; Mc: mesophyll cell; Ms: mestome sheath; Sc: sclerenchyma; Se: sieve element; Ve: vessel element. (C1) longitudinal sections of leaves; (C2) a LRP indicated in the red box in (C1); (C3): two newly initiated LRP from a crown root; (C4): cross section of crown roots; (C5): crown root tip indicated in the green box in (C1); (C6): a LRP from a primary lateral root of a crown root; (C7): a LRP from a primary lateral root. Asterisk indicates GUS is also expressed in cortex and exodermis cells nearby LRP. Abbreviation for root tissues: C: cortex; Crc: columella root cap; En: endodermis; Ep: epidermis; Ex: exodermis; Lrc: lateral root cap; LRP: lateral root primorida; Mx: metaxylem vessel; P, pericycle; Pc: procambium; QC: quiescent center; Sc: sclerenchyma.
Figure 3:
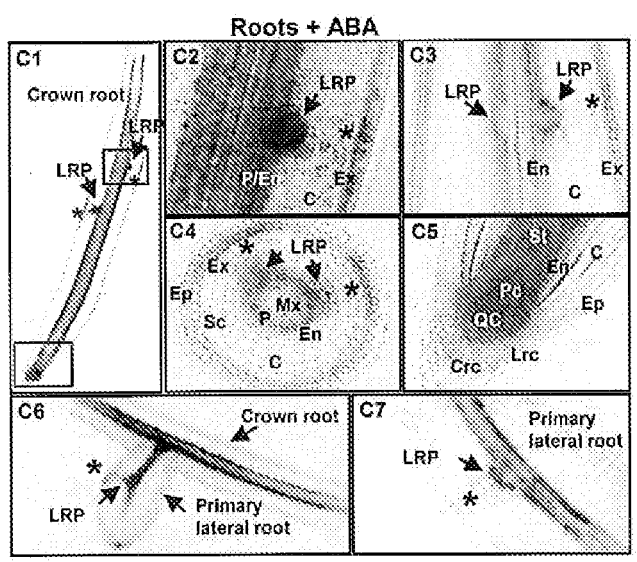

According to the staining results, in leaves, GUS controlled by 3xABRC321 was weakly expressed in phloems without ABA. (FIG. 3, B1 and B2), but strongly expressed in phloems, particularly in the companion cells and mesophyll cells after ABA treatment (FIG. 3, B3 and B4). In roots, GUS was barely detectable without ABA, but was detected at high levels mainly in lateral root primordia (LRP), pericycle and endodermis of developing roots (FIG. 3, C1-C4), and in stele, procambium and quiescent center of root tip after ABA treatment (FIG. 3, C1 and C5). GUS was also detected in the cortex and exodermis nearby the developing LRP derived from the crown and primary lateral roots treated with ABA (FIG. 3, C1-C4, C6 and C7).

2.2 HVA1 Expression Regulated by 3xABRC321 has Similar Tissue-Specificity and at Higher-Level than the Endogenous HVA1 in Transgenic Rice in Response to ABA.

Figure 4:
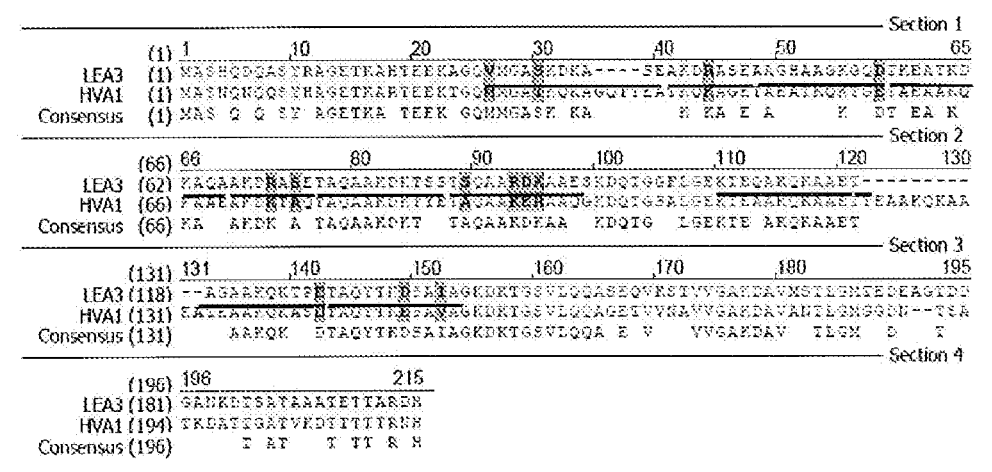
Figure 5:
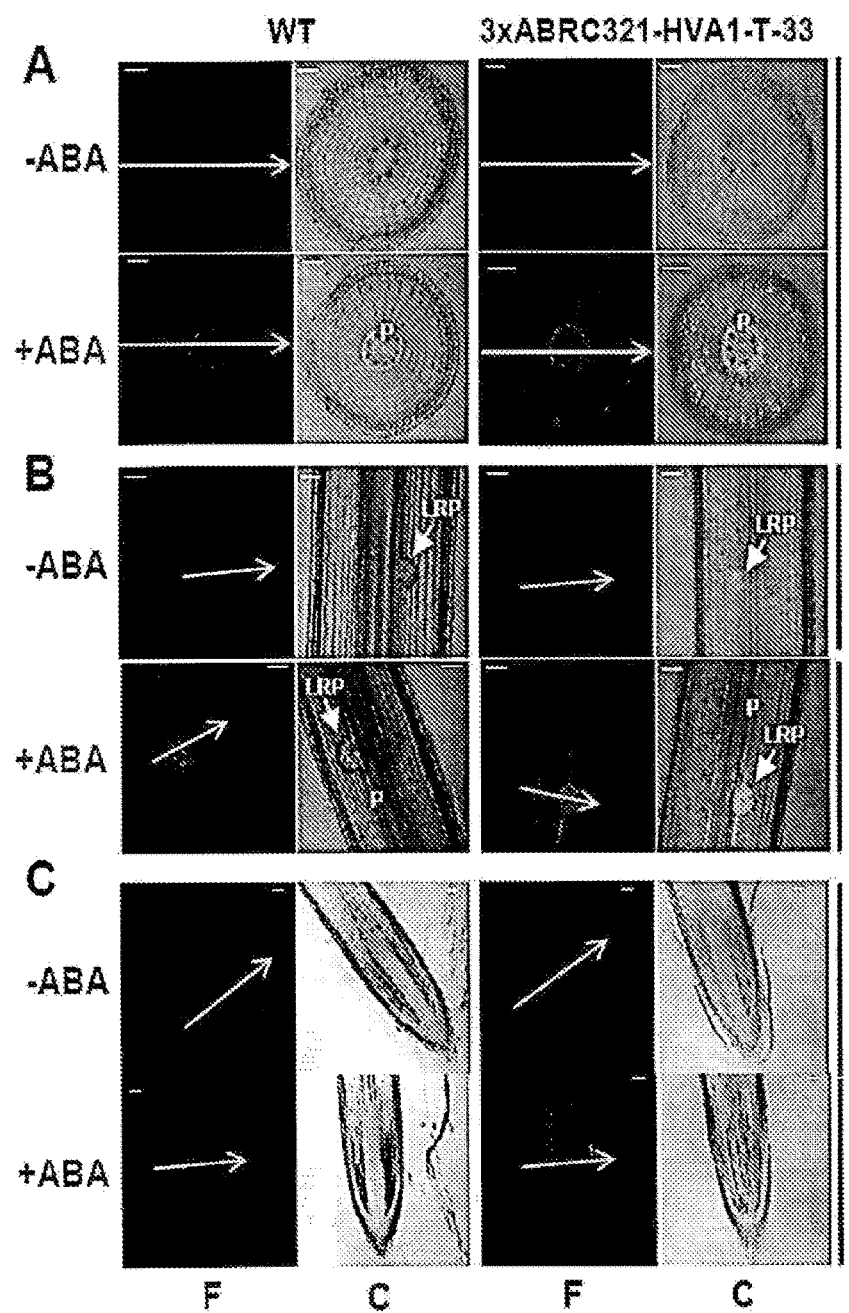
FIG. 5 shows that rHVA1 expression regulated by 3xABRC321 has similar tissue-specificity but at higher-level than the endogenous HVA1 in transgenic rice in response to ABA. (A) Cross sections of root elongation zone. (B) Longitudinal sections of root elongation zone. (C) Longitudinal sections of root tip. F: image of fluorescence field. C: composite images of fluorescence and transmission fields. P: pericycle. Scale bar represents 50 mm.

The highly ABA-inducible 3xABRC321 was used to control the expression of HVA1 in transgenic rice. The expression pattern of recombinant HVA1 (rHVA1) and the rice HVA1 homolog (Lea3) in wild type (WT) and transgenic rice roots was examined by immunocytochemistry assays using the anti-barley HVA1 antibodies, likely due to high homology of amino acid sequences between the rice Lea3 and barley HVA1s (see FIG. 4). The accumulation of Lea3 in WT and rHVA1 in transgenic rice was barely detectable in roots without ABA treatment, but was significantly increased in pericycle and endodermis and slightly increased in cortex and exodermis of roots treated with ABA (FIG. 5A). The Lea3 and rHVA1 were also detected in lateral root primordia (LRP) (FIG. 5B) and in stele, procambium and quiescent center in root tips (FIG. 5C), and levels were all increased by ABA. The accumulation of rHVA1 was significantly higher than the Lea3 prior to and after ABA treatment.

2.3 3xABRC321:HVA1 Induces Root Growth in Different Conditions.

Figure 6:
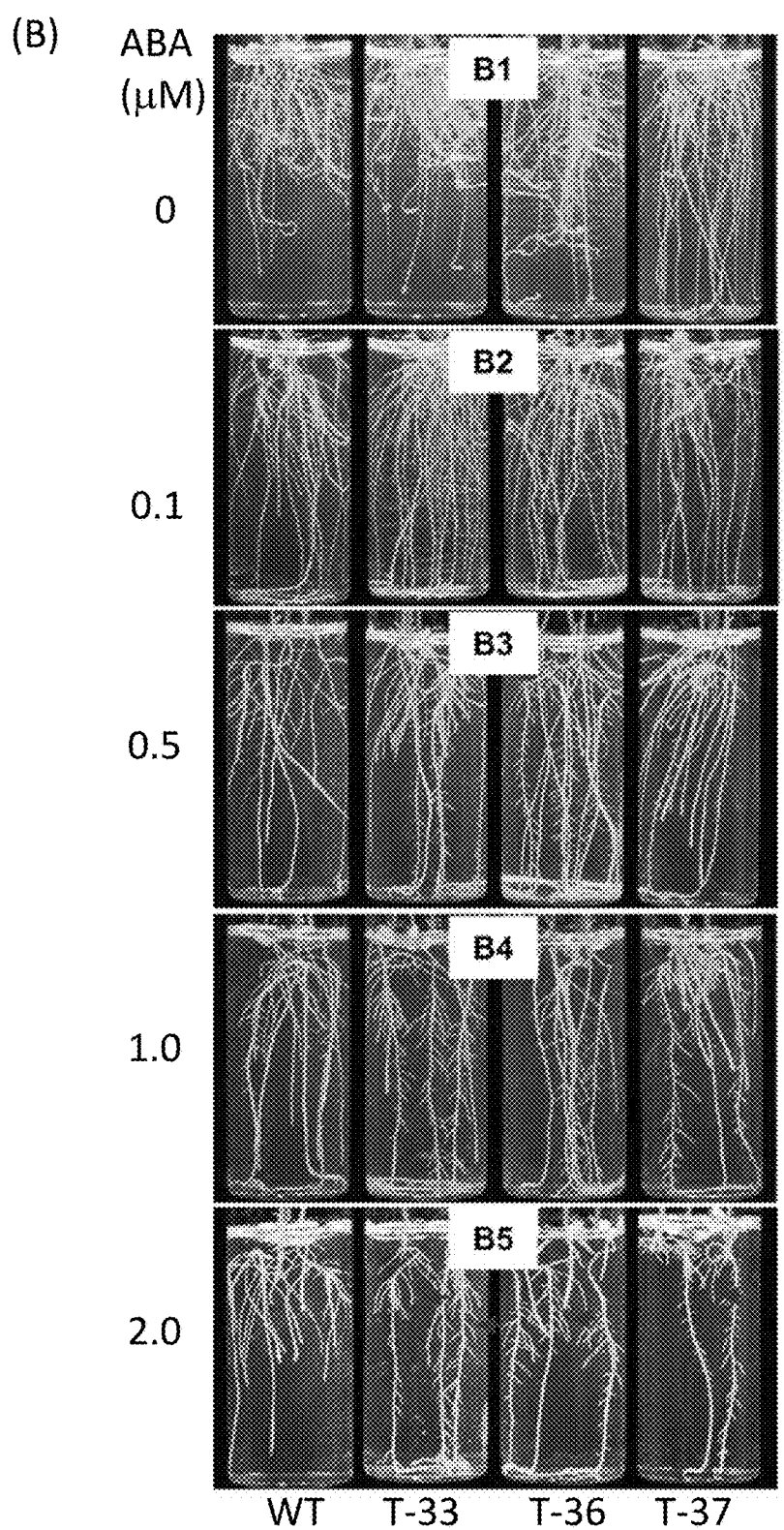
FIG. 6 shows 3xABRC321:HVA1 induces lateral root growth in transgenic rice in the presence of ABA. Three-day-old seedlings of Tainung 67 (T) transgenic lines were transferred to half-strength MS medium without sugar but containing ABA or sorbitol, and root morphology was examined. (A) Morphology of various branch roots. (B) Treatments with 0.1-2.0 μM ABA for 14 days, wherein the growth of secondary lateral roots (arrowheads) was observed in transgenic seedlings treated with 2.0 μM ABA.
Figure 7:
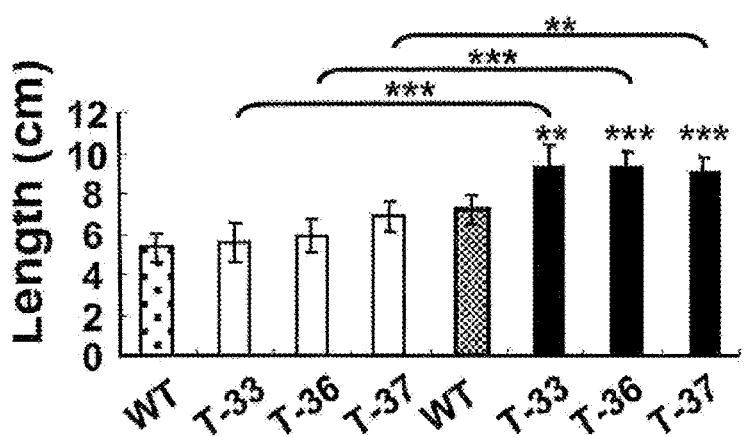
FIG. 7 shows 3xABRC321:HVA1 induces root growth in transgenic rice at ABA concentration of 0.1 μM. Left panel: crown and adventitious roots. Right panel: seminal root.
Figure 7:
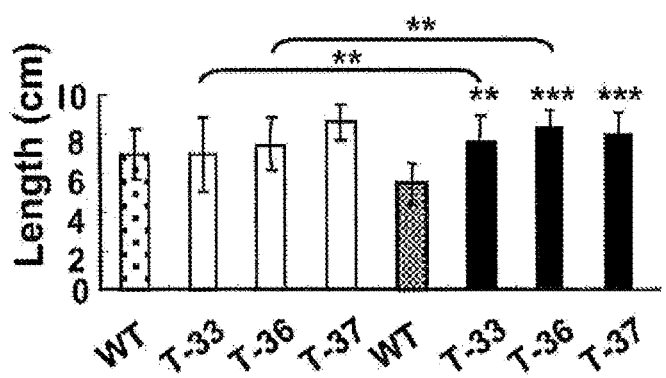

The rice line, Tainung 67, seedlings were grown in agar medium containing various concentrations of ABA. Rice contains seminal, crown, adventitious and lateral roots (FIG. 6(A)) that were longer and lateral root density was greater in three transgenic lines even without ABA treatment (FIG. 6(B), panel 1), and were all significantly increased at ABA concentrations of 0.1 μM (see the quantitative results, FIG. 7). However, lateral roots became shorter and thicker and root density decreased with ABA concentrations higher than 0.5 M (FIG. 6 (B), panels 3-5). Importantly, all root systems were longer and lateral root density was greater in transgenic lines than wild type (WT) at all ABA concentrations. Secondary lateral roots were observed only in transgenic lines with ABA concentration of 2 μM (FIG. 6(B), panel 5). Similar results were also observed in roots of transgenic rice cultivar Kitaake (data not shown).

Figure 8:
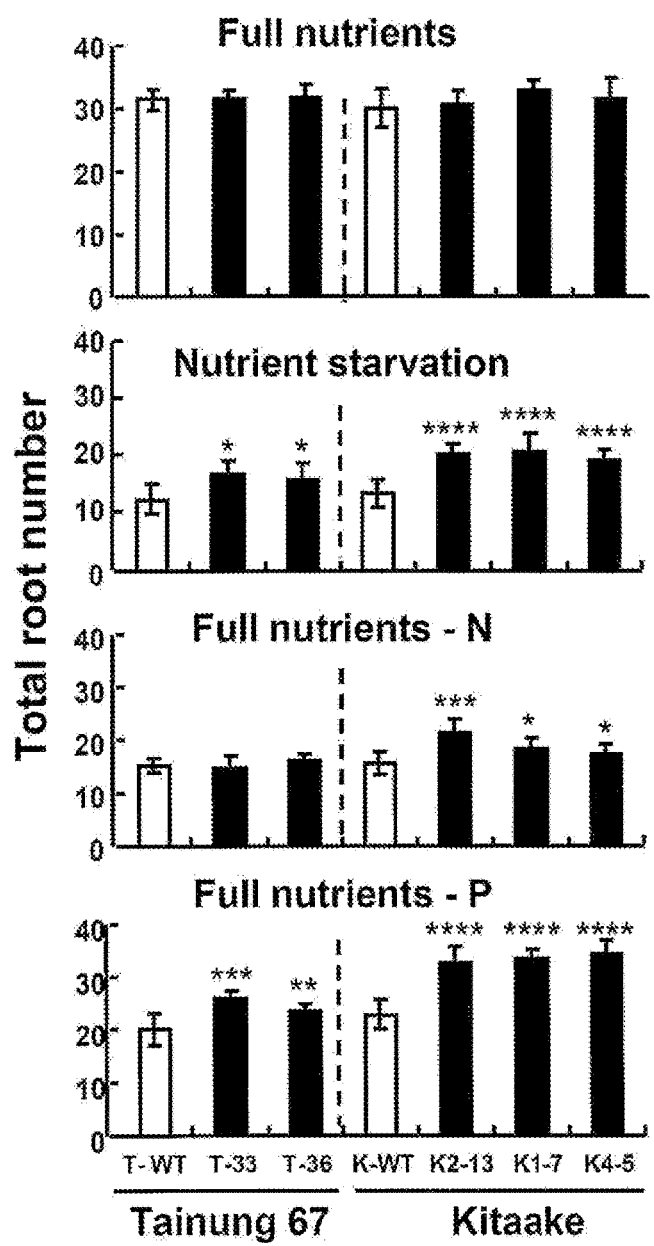
FIG. 8 shows that expression of 3xABRC321:HVA1 induces root growth in transgenic lines under nutrient deficient conditions. Four-day-old seedlings of Tainung 67 (T) and Kitaake (K) transgenic lines were germinated on MS medium for four days and transfer to full strength Yoshida solution containing full nutrients, nutrients diluted 10,000-fold (nutrient starvation), full nutrients minus nitrogen (N), and full nutrients minus phosphorus (P) for 21 days. (A) Root morphology. (B) Lateral root density. (C) Total root number.
Figure 9:
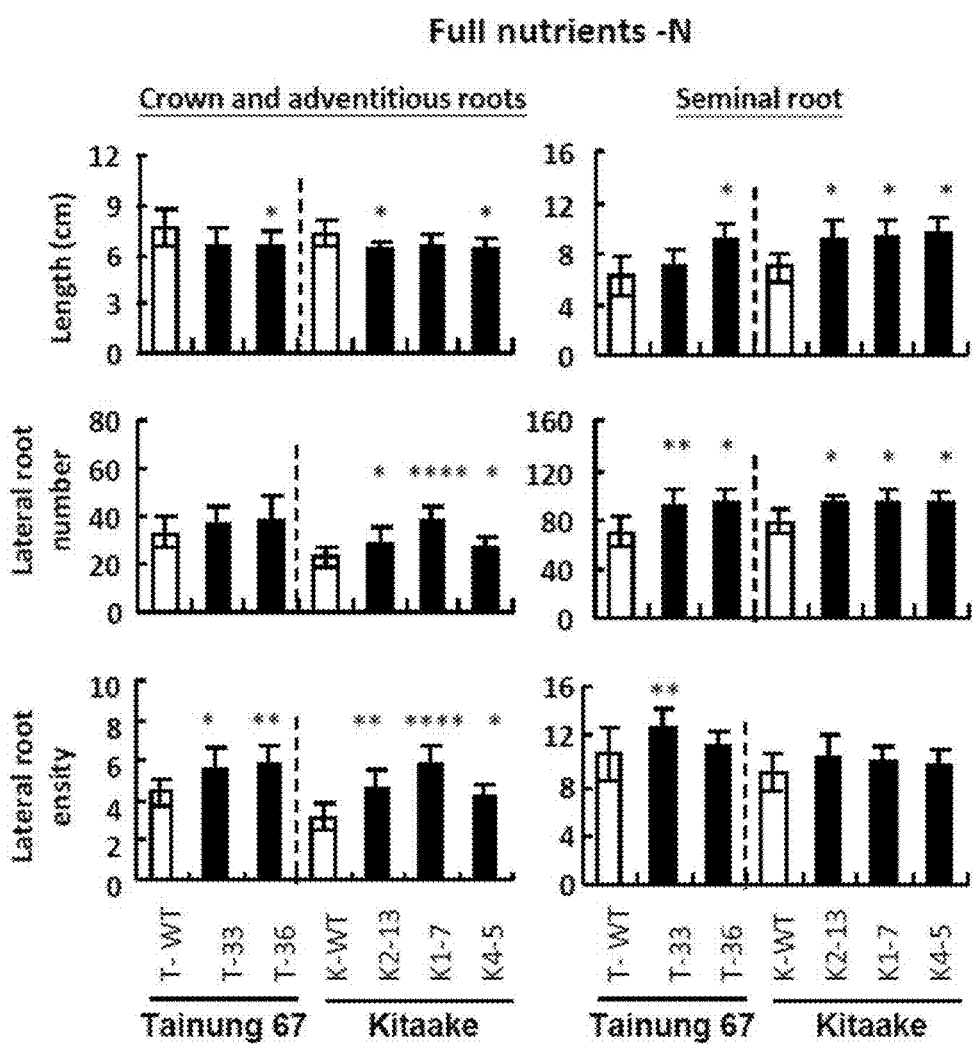
FIG. 9 shows that rHVA1 expression controlled by 3xABRC321 induces root growth in transgenic lines under nutrient deficiency. Three-day-old seedlings of Tainung 67 (T) or Kitaake (K) wild type (WT) and transgenic lines were transferred to Yoshida solutions containing (A) full nutrients, (B) nutrients diluted 10,000-fold (nutrient starvation), (C) full nutrients minus nitrogen (N), and (D) full nutrients minus phosphorus (P) for 18 days. Left panel: crown ad adventitious roots. Right panel: seminal root. Significance levels: *P<0.05, P<0.01, *P<0.001.
Figure 9:
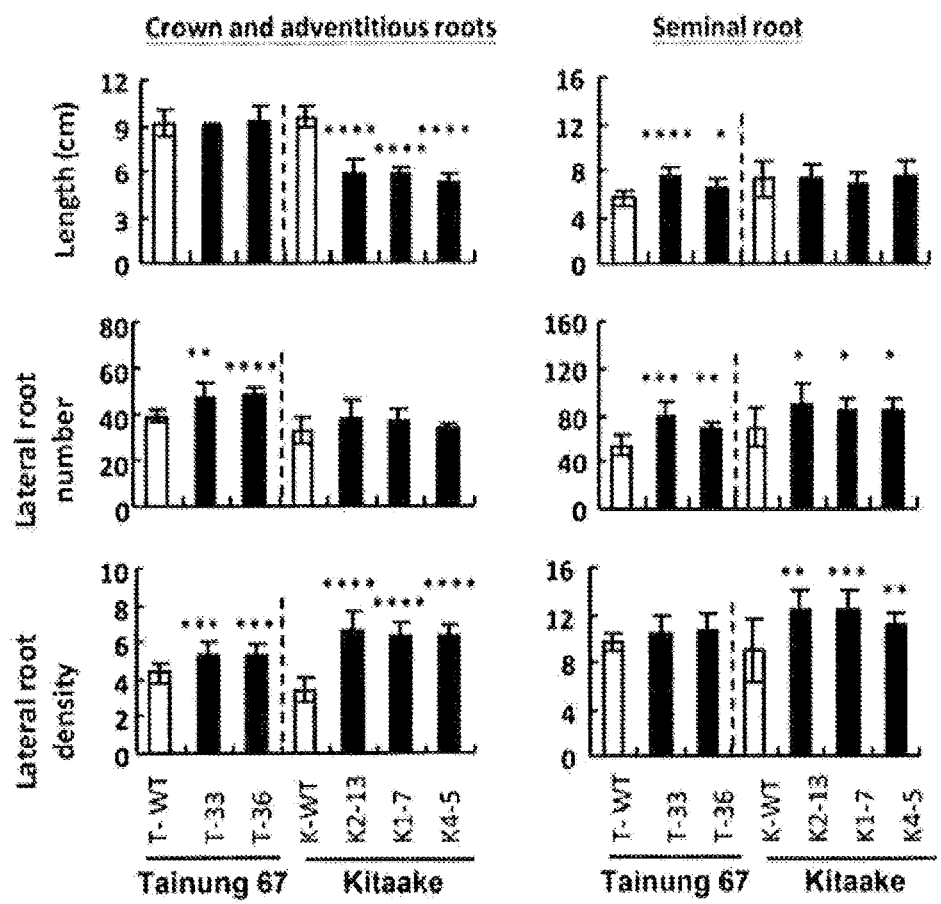

Root growth of cultivars Tainung 67 and Kitaake transgenic lines were also examined under nutrient deficient conditions. FIG. 8 (A) shows the root morphology. Total root number (FIG. 8 (C)) and root length, lateral root number, and lateral root density (FIG. 8(B) and FIG. 9 (A)-(D)) of different root systems were not significantly different when seedlings were grown with full nutrients, but were generally greater under nutrient starvation or full nutrients without nitrogen or phosphate.

Figure 10:
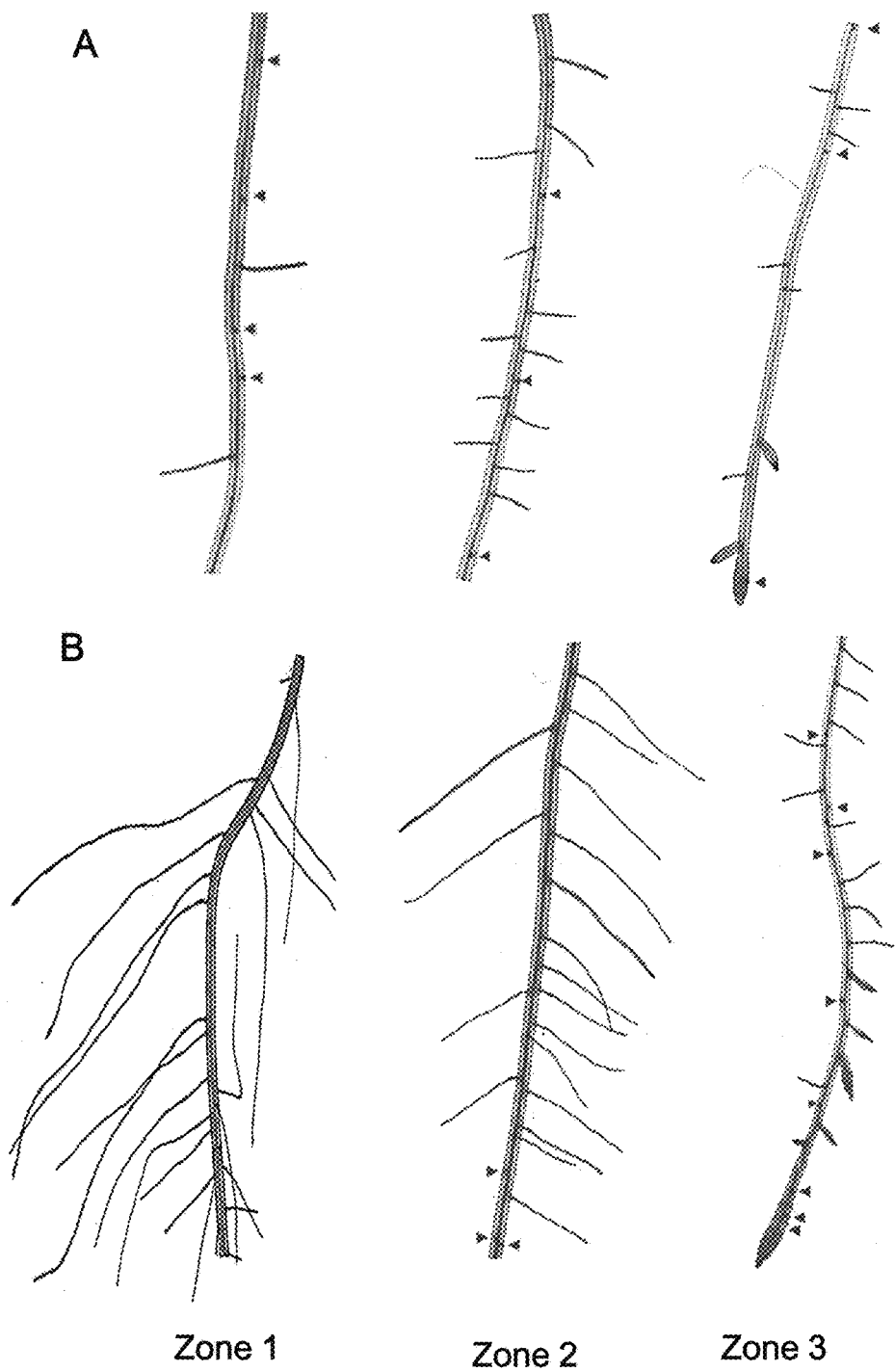
FIG. 10 shows that 3xABRC321:HVA1 promote lateral root initiation and growth in transgenic rice. Three-day-old seedlings of Tainung 67 (T) transgenic lines were transferred to half-strength MS (½) medium without sugar but containing 0.2 μM ABA for 11 days. Roots were treated with ethanol and the number of lateral root primordia (LRP) and lateral roots (LR) in three different zones were counted under microscope. Zone 1 (upper part) and Zone 2 (medium part) cover maturation zone and Zone 3 (bottom part) covers elongation and division zones of the root system. (A) Wild type plans. (B) The transgenic plants. Error bars represent SD (n=12). Significance levels: *P<0.05, P<0.01, *P<0.001.

2.4 3xABRC321:HVA1 Promotes Root Elongation and Lateral Root Initiation in Transgenic Rice Involves an Auxin-Dependent Pathway To understand whether HVA1 promotes lateral root initiation and/or elongation, root systems of seedlings treated with ABA for 11 days were examined. As shown in FIG. 10 (A)-(B), the number of lateral root primordium (LRP) was reduced but lateral roots increased in zone 1 (upper part) and zone 2 (middle part), that both cover the maturation zones, in transgenic lines as compared with WT, indicating that the majority of lateral roots initiated in transgenic lines were elongated in transgenic lines. The number of LRP and lateral root elongated were both greater in zone 3 (bottom part), which convers elongation and division zones, in transgenic lines than in WT. These results indicate that HVA1 promotes lateral root initiation and the primary root.

Figure 11:
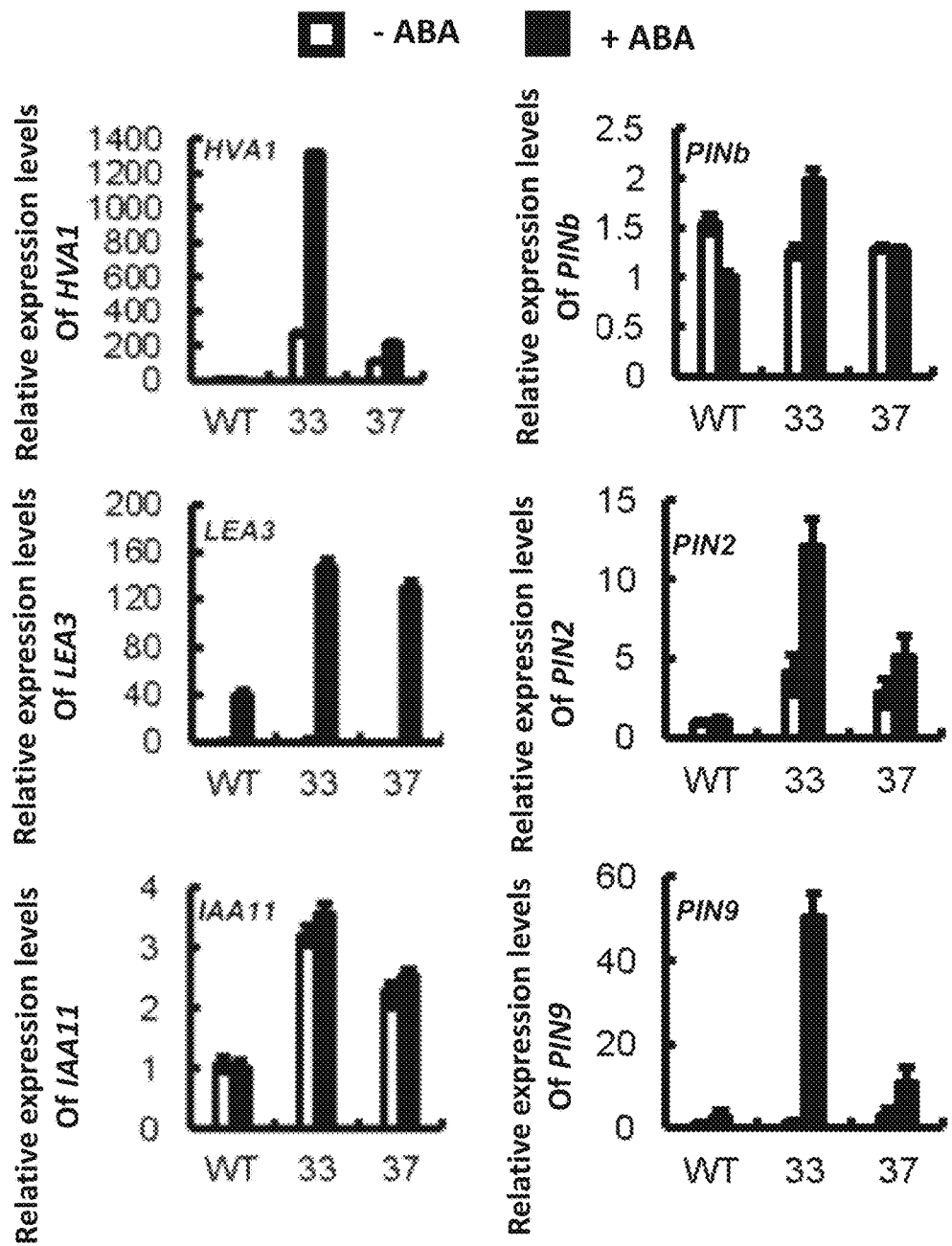
FIG. 11 shows that auxin transporters are up-regulated in 3xABRC321:HVA1 transgenic rice. Four-day-old seedlings of Tainung 67 (T) transgenic lines were germinated on MS medium for four days and transfer to full strength Yoshida solution with or without 0.2 μM ABA for 14 days. Total RNA was extracted from roots and subjected to quantitative real-time RT-PCR.

To determine whether the promotion of root growth by HVA1 in transgenic rice involves the auxin (IAA)-dependent pathway, the expression of various genes involved in auxin transport and signaling were determined. PIN proteins play a key role in auxin efflux from cells and have been shown to be involved in lateral root formation in cereals (Orman-Ligeza B, et al. (2013) Post-embryonic root organogenesis in cereals: branching out from model plants. *Trends Plant Sci* 18(8):459-467). The rice PIN family is encoded by 12 genes, with expression of each being spatially and temporally regulated (Wang J R, et al. (2009) *Mol Plant* 2(4):823-831). Real-time quantitative RT-PCR analysis revealed that expression of several PIN genes was up-regulated by ABA as well as by overexpression of HVA1 in transgenic rice (FIG. 11).

Figure 12:
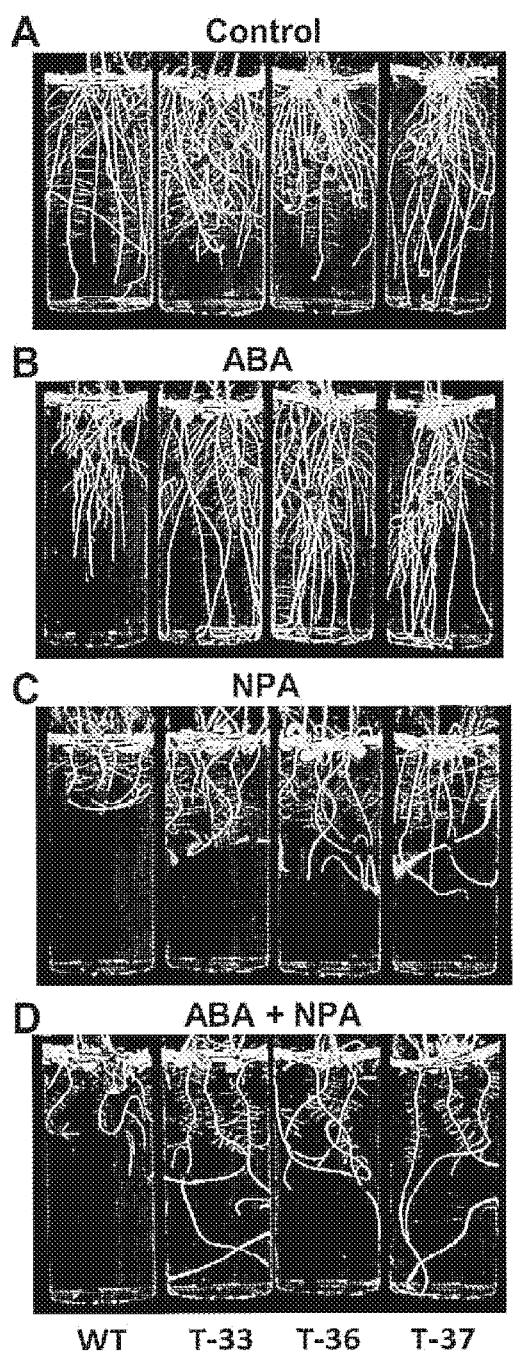
FIG. 12 shows that induction of root growth by 3xABRC321:HVA1 in the presence ABA requires auxin. Three-day-old seedlings of Tainung 67 (T) transgenic lines that containing seminal roots only were transferred to half-strength MS (½) medium without sugar but containing ABA and/or NPA for 11 days, and root morphology was examined. (A) Medium only, (B) 0.2 μM ABA only, (C) 1 μM NPA only, (D) 0.2 μM ABA plus 1 μM NPA. The dots indicate starting points of root growth after transferring to MS medium containing ABA and/or NPA.

To further demonstrate that auxin is involved for the ABA-induced root growth, 3-day-old rice seedlings with seminal roots only were transferred to medium containing ABA, with or without the polar auxin transport inhibitor N-(1-naphthyl) phtalamic acid (NPA) (Reed R C et al., (1998) *Plant Physiol* 118(4):1369-1378) for 11 days. In medium without any treatment, newly grown crown and lateral roots were more abundant in Tainung 67 transgenic lines than in WT (FIG. 12(A)). In the presence of ABA, newly grown seminal and crown roots were significantly longer and lateral roots were more abundant in transgenic lines than in WT (FIG. 12 (B)). In the presence of NPA, growth of all types of roots was inhibited (FIG. 12(C)). In the presence of both ABA and NPA, growth of crown roots and lateral roots were also inhibited except seminal roots continued to grow (FIG. 12(D)).

Figure 13:
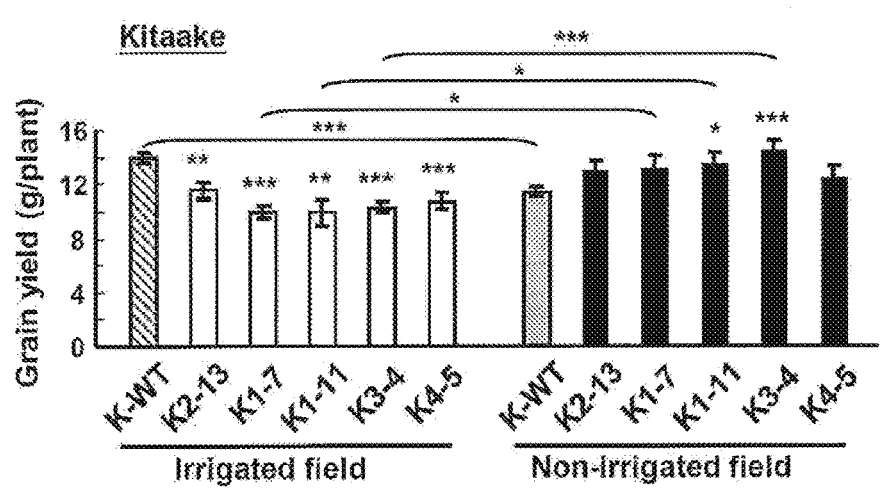
FIG. 13 shows that rHVA1 expression regulated by 3xABRC321 enhances WUE and grain yield in transgenic lines grown in non-irrigated field. (A) Three-day-old seedlings of Tainung 67 (T) and Kitaake (K) transgenic lines were treated with two cycles of 250 mM sorbitol (3 days) and water (5 days) to induce root growth. Seedlings were then grown in Yoshida solution and transferred to same amount of fresh solution every two days. Total water consumption was measured up to 19 days, and whole-plant dry weight was measured. Panel 1, dry weight of 10 plants at the end of experiment; Panel 2, total water use of 10 plants; Panel, 3, WUE determined by dividing total plant dry weight with total water use. (B) Kitaake transgenic lines were grown in irrigated and non-irrigated fields during August to December in 2011. Grain yield was determined after harvest. Error bars represent SD (n=10). Significance levels: *P<0.05, P<0.01, * P<0.001.

2.5 3xABRC321:HVA1 Enhances Water Use Efficiency (WUE) and Grain Yield in Transgenic Rice Grown in Non-Irrigated Field The WUE of transgenic Tainung 67 and Kitaake expressing rHVA1 was determined. Although transgenic lines consumed higher amounts of water (FIG. 13(A), panel 1), they produced even more biomass compared to the WT (FIG. 13(A), panel 2), thus had higher WUE than the WT (FIG. 13(A), panel 3). The performance of transgenic Kitaake grown in the field was evaluated in the fall of 2011. Rice plants were grown in two separated irrigated and non-irrigated fields, but both fields were subject to natural rainfall occasionally. Grain yield in transgenic lines was lower than WT in irrigated field, but was generally higher than WT in non-irrigated field, and surprisingly, the grain yield in transgenic lines was generally higher in non-irrigated field than in irrigated field (FIG. 13(B)). The result indicates that transgenic plants adapted the non-irrigated but naturally rain-fed field better than WT.

III. Conclusions

In this study, we found that in transgenic rice with HVA1 (the LEA3 protein in barley), the accumulation of the LEA3 protein is highly inducible by ABA, accumulated in root apical meristem and lateral root primordia (LRP), and the expansion of primary and branch root systems is significantly enhanced by ABA (especially at low concentration) and also by nutrient deficiency. We also found that the root elongation and lateral root initiation in the LEA3 protein transgenic plants involves an auxin-dependent pathway. Furthermore, the water use efficiency, biomass production, and grain yield in non-irrigated field is also increased. Our study demonstrates a successful application of transformation of plants with LEA3 gene, especially expressed by a highly active and root-specific promoter, 3xABRC321, in promoting root growth of plants, leading to advantages of at least better water use efficiency, biomass production, and grain yield.

What is claimed is:

1. A method for enhancing root growth of a plant, comprising
   (i) introducing a polynucleotide encoding a group 3 late embryogenesis abundant (LEA3) protein into plant cells to obtain transformed plant cells, wherein the polynucleotide is operably linked to an expression control sequence, and wherein the LEA3 protein comprises the amino acid sequence of SEQ ID NO: 4,
   (ii) regenerating transformed plants from said transformed plant cells; and
   (iii) selecting from said transformed plants a transformed plant exhibiting improved root growth as compared to a non-transformed control plant.

2. The method of claim 1, wherein the expression control sequence comprises a promoter sequence.

3. The method of claim 2, wherein the promoter sequence is selected from the group consisting of SEQ ID NO: 1, SEQ ID NO: 2 and SEQ ID NO: 3.

4. The method of claim 1, wherein the transformed plant exhibits improved root growth as compared to the control plant, in the presence or absence of abscisic acid (ABA).

5. The method of claim 4, wherein the transformed plant exhibits improved root growth as compared to the control plant in the presence of ABA at a concentration from 0.1 to 5 µM.

6. The method of claim 4, wherein the transformed plant exhibits improved root growth as compared to the control plant in the presence of ABA at a concentration from 0.1 to 2 µM.

7. The method of claim 4, wherein the transformed plant exhibits improved root growth as compared to the control plant in the presence of ABA at a concentration of from 0.1 to 0.5 µM.

8. The method of claim 1, wherein the transformed plant exhibits improved root growth as compared to the control plant under nutrient deficient conditions.

9. The method of claim 1, wherein the transgenic plant is a monocotyledon plant or a dicotyledon plant.

10. The method of claim 9, wherein the monocotyledon plant is selected from the group consisting of rice, barley, wheat, rye, oat, corn, bamboo, sugar cane, onion, leek and ginger.

11. The method of claim 9, wherein the plant is a monocotyledon plant, which is rice.

12. The method of claim 9, wherein the dicotyledon plant is selected from the group consisting of *Arabidopsis*, eggplant, soybean, mung bean, kidney bean, pea, tobacco, lettuce, spinach, sweet potato, carrot, melon, cucumber and pumpkin.

* * * * *

SEQUENCE LISTING

```
<160> NUMBER OF SEQ ID NOS: 7

<210> SEQ ID NO 1
<211> LENGTH: 56
<212> TYPE: DNA
<213> ORGANISM: Artificial Sequence
<220> FEATURE:
<223> OTHER INFORMATION: Synthetic promoter 1XABRC321

<400> SEQUENCE: 1
ggtaccgcaa cgcgtgtcct ccctacgtgg cggctcgaga ttgccaccgg tctaga        56

<210> SEQ ID NO 2
<211> LENGTH: 106
<212> TYPE: DNA
<213> ORGANISM: Artificial Sequence
<220> FEATURE:
<223> OTHER INFORMATION: Synthetic promoter 2XABRC321

<400> SEQUENCE: 2
ggtaccgcaa cgcgtgtcct ccctacgtgg cggctcgaga ttgccaccgg ggtaccgcaa    60
cgcgtgtcct ccctacgtgg cggctcgaga ttgccaccgg tctaga                  106

<210> SEQ ID NO 3
<211> LENGTH: 156
<212> TYPE: DNA
<213> ORGANISM: Artificial Sequence
<220> FEATURE:
<223> OTHER INFORMATION: Synthetic prompter 3XABRC321

<400> SEQUENCE: 3
ggtaccgcaa cgcgtgtcct ccctacgtgg cggctcgaga ttgccaccgg ggtaccgcaa    60
cgcgtgtcct ccctacgtgg cggctcgaga ttgccaccgg ggtaccgcaa cgcgtgtcct   120
ccctacgtgg cggctcgaga ttgccaccgg tctaga                             156

<210> SEQ ID NO 4
```

```
<211> LENGTH: 213
<212> TYPE: PRT
<213> ORGANISM: Hordeum vulgare

<400> SEQUENCE: 4
```

Met Ala Ser Asn Gln Asn Gln Gln Ser Tyr His Ala Gly Glu Thr Lys
1               5                   10                  15

Ala Arg Thr Glu Glu Lys Thr Gly Gln Met Met Gly Ala Thr Lys Gln
            20                  25                  30

Lys Ala Gly Gln Thr Thr Glu Ala Thr Lys Gln Lys Ala Gly Glu Thr
        35                  40                  45

Ala Glu Ala Thr Lys Gln Lys Thr Gly Glu Thr Ala Glu Ala Ala Lys
    50                  55                  60

Gln Lys Ala Ala Glu Ala Lys Asp Lys Thr Ala Gln Thr Ala Gln Ala
65                  70                  75                  80

Ala Lys Asp Lys Thr Tyr Glu Thr Ala Gln Ala Ala Lys Glu Arg Ala
                85                  90                  95

Ala Gln Gly Lys Asp Gln Thr Gly Ser Ala Leu Gly Glu Lys Thr Glu
            100                 105                 110

Ala Ala Lys Gln Lys Ala Ala Glu Thr Thr Glu Ala Ala Lys Gln Lys
        115                 120                 125

Ala Ala Glu Ala Thr Glu Ala Ala Lys Gln Lys Ala Ser Asp Thr Ala
    130                 135                 140

Gln Tyr Thr Lys Glu Ser Val Ala Gly Lys Asp Lys Thr Gly Ser
145                 150                 155                 160

Val Leu Gln Gln Ala Gly Glu Thr Val Val Asn Ala Val Gly Ala
                165                 170                 175

Lys Asp Ala Val Ala Asn Thr Leu Gly Met Gly Gly Asp Asn Thr Ser
            180                 185                 190

Ala Thr Lys Asp Ala Thr Thr Gly Ala Thr Val Lys Asp Thr Thr Thr
        195                 200                 205

Thr Thr Arg Asn His
        210

```
<210> SEQ ID NO 5
<211> LENGTH: 200
<212> TYPE: PRT
<213> ORGANISM: Oryza sativa

<400> SEQUENCE: 5
```

Met Ala Ser His Gln Asp Gln Ala Ser Tyr Arg Ala Gly Glu Thr Lys
1               5                   10                  15

Ala His Thr Glu Glu Lys Ala Gly Gln Val Met Gly Ala Ser Lys Asp
            20                  25                  30

Lys Ala Ser Glu Ala Lys Asp Arg Ala Ser Glu Ala Ala Gly His Ala
        35                  40                  45

Ala Gly Lys Gly Gln Asp Thr Lys Glu Ala Thr Lys Asp Lys Ala Gln
    50                  55                  60

Ala Ala Lys Asp Arg Ala Ser Glu Thr Ala Gln Ala Ala Lys Asp Lys
65                  70                  75                  80

Thr Ser Ser Thr Ser Gln Ala Ala Arg Asp Lys Ala Ala Glu Ser Lys
                85                  90                  95

Asp Gln Thr Gly Gly Phe Leu Gly Glu Lys Thr Glu Gln Ala Lys Gln
            100                 105                 110

Lys Ala Ala Glu Thr Ala Gly Ala Ala Lys Gln Lys Thr Pro Glu Thr
        115                 120                 125

Ala Gln Tyr Thr Lys Asp Ser Ala Ile Ala Gly Lys Asp Lys Thr Gly
         130                 135                 140

Ser Val Leu Gln Gln Ala Ser Glu Gln Val Lys Ser Thr Val Val Gly
145                 150                 155                 160

Ala Lys Asp Ala Val Met Ser Thr Leu Gly Met Thr Glu Asp Glu Ala
                165                 170                 175

Gly Thr Asp Asp Gly Ala Asn Lys Asp Thr Ser Ala Thr Ala Ala Ala
                180                 185                 190

Thr Glu Thr Thr Ala Arg Asp His
                195                 200

<210> SEQ ID NO 6
<211> LENGTH: 1542
<212> TYPE: DNA
<213> ORGANISM: Artificial Sequence
<220> FEATURE:
<223> OTHER INFORMATION: 3xABRC321-HVA1

<400> SEQUENCE: 6

```
ggtaccgcaa cgcgtgtcct ccctacgtgg cggctcgaga ttgccaccgg ggtaccgcaa      60
cgcgtgtcct ccctacgtgg cggctcgaga ttgccaccgg ggtaccgcaa cgcgtgtcct     120
ccctacgtgg cggctcgaga ttgccaccgg tctagagtcg acctgcagca attccggcat     180
gccgcagcac actataaata cctggccaga cacacaagct gaatgcatca gttctccatc     240
gtactcttcg agagcacagc aagagagtga tcatttcagg taagatctag agtcgacctg     300
caggcgaccg tatgtatatt accctatctc taccttgcaa atcgcgtgtg tacggatctt     360
ctccgtggtc gagccgagtg attgctgatc tgatatccta tctgctgctt cgtttccttg     420
cgcaggccaa gcatcacgct gctgtaccct ctgtaagttg atcagtcgct tgtggtactt     480
tttagtacgt ggggaagtaa tccttgtgct ggatgtgacc ctggcggatc tgtataatac     540
aggtatgcgg atccaccatg gcgggtggtc agtcccttat ggcctccaac cagaaccagg     600
ggagctacca cgccggcgag accaaggccc gcaccgagga agaccgggg cagatgatgg      660
gcgccaccaa gcagaaggcg gggcagacca ccgaggccac caagcagaag gccggcgaga     720
cggccgaggc caccaagcag aagaccggcg agacggccga ggccgccaag cagaaggccg     780
ccgaggccaa ggacaagacg gcgcagacgg cgcaggcggc caaggacaag acgtacgaga     840
cggcgcaggc ggccaaggag cgcgccgccc agggcaagga ccagaccggc agcgccctcg     900
gcgagaagac ggaggcggcc aagcagaagg ccgccgagac gacggaggcg gccaagcaga     960
aggccgccga ggcaaccgag gcggccaagc agaaggcgtc cgacacggcg cagtacacca    1020
aggagtccgc ggtggccggc aaggacaaga ccggcagcgt cctccagcag gccggcgaga    1080
cggtggtgaa cgccgtggtg gcgccaagg acgccgtggc aaacacgctg gcatgggag     1140
gggacaacac cagcgccacc aaggacgcca ccaccggcgc caccgtcaag gacaccacca    1200
ccaccaccag gaatcactag atcaacaact ctcctggcgc accatcgtcg gctacagcct    1260
cgggaattgc tacagcttgc atgatcgttc aaacatttgg caataaagtt tcttaagatt    1320
gaatcctgtt gccggtcttg cgatgattat catataattt ctgttgaatt acgttaagca    1380
tgtaataatt aacatgtaat gcatgacgtt atttatgaga tgggttttta tgattagagt    1440
cccgcaatta tacatttaat acgcgataga aaacaaaata tagcgcgcaa actaggataa    1500
attatcgcgc gcggtgtcat ctatgttact agatccaagc tt                       1542
```

```
<210> SEQ ID NO 7
<211> LENGTH: 215
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa is His or Asn
<220> FEATURE:
<221> NAME/KEY: misc_feature
<222> LOCATION: (6)..(6)
<223> OTHER INFORMATION: Xaa is Asp or Asn
<220> FEATURE:
<221> NAME/KEY: misc_feature
<222> LOCATION: (8)..(8)
<223> OTHER INFORMATION: Xaa is Ala or Gln
<220> FEATURE:
<221> NAME/KEY: misc_feature
<222> LOCATION: (11)..(11)
<223> OTHER INFORMATION: Xaa is Arg or His
<220> FEATURE:
<221> NAME/KEY: misc_feature
<222> LOCATION: (18)..(18)
<223> OTHER INFORMATION: Xaa is His or Arg
<220> FEATURE:
<221> NAME/KEY: misc_feature
<222> LOCATION: (23)..(23)
<223> OTHER INFORMATION: Xaa is Ala or Thr
<220> FEATURE:
<221> NAME/KEY: misc_feature
<222> LOCATION: (32)..(32)
<223> OTHER INFORMATION: Xaa is Asp or Gln
<220> FEATURE:
<221> NAME/KEY: misc_feature
<222> LOCATION: (35)..(35)
<223> OTHER INFORMATION: Xaa is absent or Gly
<220> FEATURE:
<221> NAME/KEY: misc_feature
<222> LOCATION: (36)..(36)
<223> OTHER INFORMATION: Xaa is absent or Gln
<220> FEATURE:
<221> NAME/KEY: misc_feature
<222> LOCATION: (37)..(37)
<223> OTHER INFORMATION: Xaa is absent or Thr
<220> FEATURE:
<221> NAME/KEY: misc_feature
<222> LOCATION: (38)..(38)
<223> OTHER INFORMATION: Xaa is absent or Thr
<220> FEATURE:
<221> NAME/KEY: misc_feature
<222> LOCATION: (39)..(39)
<223> OTHER INFORMATION: Xaa is Ser or Glu
<220> FEATURE:
<221> NAME/KEY: misc_feature
<222> LOCATION: (40)..(40)
<223> OTHER INFORMATION: Xaa is Glu or Ala
<220> FEATURE:
<221> NAME/KEY: misc_feature
<222> LOCATION: (41)..(41)
<223> OTHER INFORMATION: Xaa is Ala or Thr
<220> FEATURE:
<221> NAME/KEY: misc_feature
<222> LOCATION: (43)..(43)
<223> OTHER INFORMATION: Xaa is Asp or Gln
<220> FEATURE:
<221> NAME/KEY: misc_feature
<222> LOCATION: (46)..(46)
<223> OTHER INFORMATION: Xaa is Ser or Gly
<220> FEATURE:
<221> NAME/KEY: misc_feature
<222> LOCATION: (48)..(48)
<223> OTHER INFORMATION: Xaa is Ala or Thr
<220> FEATURE:
<221> NAME/KEY: misc_feature
<222> LOCATION: (50)..(50)
<223> OTHER INFORMATION: Xaa is Gly or Glu
<220> FEATURE:
```

-continued

```
<221> NAME/KEY: misc_feature
<222> LOCATION: (51)..(51)
<223> OTHER INFORMATION: Xaa is His or Ala
<220> FEATURE:
<221> NAME/KEY: misc_feature
<222> LOCATION: (52)..(52)
<223> OTHER INFORMATION: Xaa is Ala or Thr
<220> FEATURE:
<221> NAME/KEY: misc_feature
<222> LOCATION: (53)..(53)
<223> OTHER INFORMATION: Xaa is Ala or Lys
<220> FEATURE:
<221> NAME/KEY: misc_feature
<222> LOCATION: (54)..(54)
<223> OTHER INFORMATION: Xaa is Gly or Gln
<220> FEATURE:
<221> NAME/KEY: misc_feature
<222> LOCATION: (56)..(56)
<223> OTHER INFORMATION: Xaa is Gly or Thr
<220> FEATURE:
<221> NAME/KEY: misc_feature
<222> LOCATION: (57)..(57)
<223> OTHER INFORMATION: Xaa is Gln or Gly
<220> FEATURE:
<221> NAME/KEY: misc_feature
<222> LOCATION: (60)..(60)
<223> OTHER INFORMATION: Xaa is Lys or Ala
<220> FEATURE:
<221> NAME/KEY: misc_feature
<222> LOCATION: (63)..(63)
<223> OTHER INFORMATION: Xaa is Thr or Ala
<220> FEATURE:
<221> NAME/KEY: misc_feature
<222> LOCATION: (65)..(65)
<223> OTHER INFORMATION: Xaa is Asp or Gln
<220> FEATURE:
<221> NAME/KEY: misc_feature
<222> LOCATION: (68)..(68)
<223> OTHER INFORMATION: Xaa is Gln or Ala
<220> FEATURE:
<221> NAME/KEY: misc_feature
<222> LOCATION: (69)..(69)
<223> OTHER INFORMATION: Xaa is Ala or Glu
<220> FEATURE:
<221> NAME/KEY: misc_feature
<222> LOCATION: (74)..(74)
<223> OTHER INFORMATION: Xaa is Ala or Thr
<220> FEATURE:
<221> NAME/KEY: misc_feature
<222> LOCATION: (76)..(76)
<223> OTHER INFORMATION: Xaa is Glu or Gln
<220> FEATURE:
<221> NAME/KEY: misc_feature
<222> LOCATION: (86)..(86)
<223> OTHER INFORMATION: Xaa is Ser or Tyr
<220> FEATURE:
<221> NAME/KEY: misc_feature
<222> LOCATION: (87)..(87)
<223> OTHER INFORMATION: Xaa is Ser or Glu
<220> FEATURE:
<221> NAME/KEY: misc_feature
<222> LOCATION: (98)..(98)
<223> OTHER INFORMATION: Xaa is Glu or Gln
<220> FEATURE:
<221> NAME/KEY: misc_feature
<222> LOCATION: (99)..(99)
<223> OTHER INFORMATION: Xaa is Ser or Gly
<220> FEATURE:
<221> NAME/KEY: misc_feature
<222> LOCATION: (105)..(105)
<223> OTHER INFORMATION: Xaa is Gly or Ser
<220> FEATURE:
<221> NAME/KEY: misc_feature
<222> LOCATION: (106)..(106)
<223> OTHER INFORMATION: Xaa is Phe or Ala
<220> FEATURE:
<221> NAME/KEY: misc_feature
<222> LOCATION: (113)..(113)
<223> OTHER INFORMATION: Xaa is Gln or Ala
```

```
<220> FEATURE:
<221> NAME/KEY: misc_feature
<222> LOCATION: (122)..(122)
<223> OTHER INFORMATION: Xaa is absent or Thr
<220> FEATURE:
<221> NAME/KEY: misc_feature
<222> LOCATION: (123)..(123)
<223> OTHER INFORMATION: Xaa is absent or Glu
<220> FEATURE:
<221> NAME/KEY: misc_feature
<222> LOCATION: (124)..(125)
<223> OTHER INFORMATION: Xaa is absent or Ala
<220> FEATURE:
<221> NAME/KEY: misc_feature
<222> LOCATION: (126)..(126)
<223> OTHER INFORMATION: Xaa is absent or Lys
<220> FEATURE:
<221> NAME/KEY: misc_feature
<222> LOCATION: (127)..(127)
<223> OTHER INFORMATION: Xaa is absent or Gln
<220> FEATURE:
<221> NAME/KEY: misc_feature
<222> LOCATION: (128)..(128)
<223> OTHER INFORMATION: Xaa is absent or Lys
<220> FEATURE:
<221> NAME/KEY: misc_feature
<222> LOCATION: (129)..(130)
<223> OTHER INFORMATION: Xaa is absent or Ala
<220> FEATURE:
<221> NAME/KEY: misc_feature
<222> LOCATION: (131)..(131)
<223> OTHER INFORMATION: Xaa is absent or Glu
<220> FEATURE:
<221> NAME/KEY: misc_feature
<222> LOCATION: (132)..(132)
<223> OTHER INFORMATION: Xaa is absent or Ala
<220> FEATURE:
<221> NAME/KEY: misc_feature
<222> LOCATION: (133)..(133)
<223> OTHER INFORMATION: Xaa is Ala or Thr
<220> FEATURE:
<221> NAME/KEY: misc_feature
<222> LOCATION: (134)..(134)
<223> OTHER INFORMATION: Xaa is Gly or Glu
<220> FEATURE:
<221> NAME/KEY: misc_feature
<222> LOCATION: (140)..(140)
<223> OTHER INFORMATION: Xaa is Thr or Ala
<220> FEATURE:
<221> NAME/KEY: misc_feature
<222> LOCATION: (141)..(141)
<223> OTHER INFORMATION: Xaa is Pro or Ser
<220> FEATURE:
<221> NAME/KEY: misc_feature
<222> LOCATION: (166)..(166)
<223> OTHER INFORMATION: Xaa is Ser or Gly
<220> FEATURE:
<221> NAME/KEY: misc_feature
<222> LOCATION: (168)..(168)
<223> OTHER INFORMATION: Xaa is Gln or Thr
<220> FEATURE:
<221> NAME/KEY: misc_feature
<222> LOCATION: (170)..(170)
<223> OTHER INFORMATION: Xaa is Lys or Val
<220> FEATURE:
<221> NAME/KEY: misc_feature
<222> LOCATION: (171)..(171)
<223> OTHER INFORMATION: Xaa is Ser or Asn
<220> FEATURE:
<221> NAME/KEY: misc_feature
<222> LOCATION: (172)..(172)
<223> OTHER INFORMATION: Xaa is Thr or Ala
<220> FEATURE:
<221> NAME/KEY: misc_feature
<222> LOCATION: (181)..(181)
<223> OTHER INFORMATION: Xaa is Met or Ala
<220> FEATURE:
<221> NAME/KEY: misc_feature
<222> LOCATION: (182)..(182)
```

```
<223> OTHER INFORMATION: Xaa is Ser or Asn
<220> FEATURE:
<221> NAME/KEY: misc_feature
<222> LOCATION: (187)..(187)
<223> OTHER INFORMATION: Xaa is Thr or Gly
<220> FEATURE:
<221> NAME/KEY: misc_feature
<222> LOCATION: (188)..(188)
<223> OTHER INFORMATION: Xaa is Glu or Gly
<220> FEATURE:
<221> NAME/KEY: misc_feature
<222> LOCATION: (190)..(190)
<223> OTHER INFORMATION: Xaa is Glu or Asn
<220> FEATURE:
<221> NAME/KEY: misc_feature
<222> LOCATION: (191)..(191)
<223> OTHER INFORMATION: Xaa is Ala or absent
<220> FEATURE:
<221> NAME/KEY: misc_feature
<222> LOCATION: (192)..(192)
<223> OTHER INFORMATION: Xaa is Gly or absent
<220> FEATURE:
<221> NAME/KEY: misc_feature
<222> LOCATION: (194)..(194)
<223> OTHER INFORMATION: Xaa is Asp or Ser
<220> FEATURE:
<221> NAME/KEY: misc_feature
<222> LOCATION: (195)..(195)
<223> OTHER INFORMATION: Xaa is Asp or Ala
<220> FEATURE:
<221> NAME/KEY: misc_feature
<222> LOCATION: (196)..(196)
<223> OTHER INFORMATION: Xaa is Gly or Thr
<220> FEATURE:
<221> NAME/KEY: misc_feature
<222> LOCATION: (197)..(197)
<223> OTHER INFORMATION: Xaa is Ala or Lys
<220> FEATURE:
<221> NAME/KEY: misc_feature
<222> LOCATION: (198)..(198)
<223> OTHER INFORMATION: Xaa is Asn or Asp
<220> FEATURE:
<221> NAME/KEY: misc_feature
<222> LOCATION: (199)..(199)
<223> OTHER INFORMATION: Xaa is Lys or Ala
<220> FEATURE:
<221> NAME/KEY: misc_feature
<222> LOCATION: (200)..(200)
<223> OTHER INFORMATION: Xaa is Asp or Thr
<220> FEATURE:
<221> NAME/KEY: misc_feature
<222> LOCATION: (202)..(202)
<223> OTHER INFORMATION: Xaa is Ser or Gly
<220> FEATURE:
<221> NAME/KEY: misc_feature
<222> LOCATION: (205)..(205)
<223> OTHER INFORMATION: Xaa is Ala or Val
<220> FEATURE:
<221> NAME/KEY: misc_feature
<222> LOCATION: (206)..(206)
<223> OTHER INFORMATION: Xaa is Ala or Lys
<220> FEATURE:
<221> NAME/KEY: misc_feature
<222> LOCATION: (207)..(207)
<223> OTHER INFORMATION: Xaa is Ala or Asp
<220> FEATURE:
<221> NAME/KEY: misc_feature
<222> LOCATION: (209)..(209)
<223> OTHER INFORMATION: Xaa is Glu or Thr
<220> FEATURE:
<221> NAME/KEY: misc_feature
<222> LOCATION: (212)..(212)
<223> OTHER INFORMATION: Xaa is Ala or Thr
<220> FEATURE:
<221> NAME/KEY: misc_feature
<222> LOCATION: (214)..(214)
<223> OTHER INFORMATION: Xaa is Asp or Asn

<400> SEQUENCE: 7
```

```
-continued

Met Ala Ser Xaa Gln Xaa Gln Xaa Ser Tyr Xaa Ala Gly Glu Thr Lys
1               5                   10                  15

Ala Xaa Thr Glu Glu Lys Xaa Gly Gln Met Met Gly Ala Ser Lys Xaa
            20                  25                  30

Lys Ala Xaa Xaa Xaa Xaa Xaa Xaa Lys Xaa Lys Ala Xaa Glu Xaa
            35                  40                  45

Ala Xaa Xaa Xaa Xaa Xaa Lys Xaa Xaa Asp Thr Xaa Glu Ala Xaa Lys
    50                  55                  60

Xaa Lys Ala Xaa Xaa Ala Lys Asp Lys Xaa Ala Xaa Thr Ala Glu Ala
65              70                  75                  80

Ala Lys Asp Lys Thr Xaa Xaa Thr Ala Gln Ala Ala Lys Asp Lys Ala
            85                  90                  95

Ala Xaa Xaa Lys Asp Gln Thr Gly Xaa Xaa Leu Gly Glu Lys Thr Glu
            100                 105                 110

Xaa Ala Lys Gln Lys Ala Ala Glu Thr Xaa Xaa Xaa Xaa Xaa Xaa Xaa
        115                 120                 125

Xaa Xaa Xaa Xaa Xaa Xaa Ala Ala Lys Gln Lys Xaa Xaa Asp Thr Ala
    130                 135                 140

Gln Tyr Thr Lys Asp Ser Ala Ile Ala Gly Lys Asp Lys Thr Gly Ser
145             150                 155                 160

Val Leu Gln Gln Ala Xaa Glu Xaa Val Xaa Xaa Xaa Val Val Gly Ala
            165                 170                 175

Lys Asp Ala Val Xaa Xaa Thr Leu Gly Met Xaa Xaa Asp Xaa Xaa Xaa
            180             185                 190

Thr Xaa Xaa Xaa Xaa Xaa Xaa Thr Xaa Ala Thr Xaa Xaa Xaa Thr
    195                 200                 205

Xaa Thr Thr Xaa Arg Xaa His
    210             215
```